United States Patent
Hall et al.

(10) Patent No.: US 9,107,723 B2
(45) Date of Patent: Aug. 18, 2015

(54) SYSTEM AND METHOD FOR THE DESIGN, CREATION AND INSTALLATION OF IMPLANT-SUPPORTED DENTAL PROSTHESES

(75) Inventors: Benson Luther Hall, Midlothain, VA (US); Walter Raleigh Beam, Chester, VA (US)

(73) Assignee: BENSON LUTHER HALL, Richmond, VA (US)

( * ) Notice: Subject to any disclaimer, the term of this patent is extended or adjusted under 35 U.S.C. 154(b) by 1255 days.

(21) Appl. No.: 11/562,953

(22) Filed: Nov. 22, 2006

(65) Prior Publication Data

US 2007/0154866 A1 Jul. 5, 2007

Related U.S. Application Data

(60) Provisional application No. 60/738,516, filed on Nov. 22, 2005, provisional application No. 60/828,064, filed on Oct. 3, 2006.

(51) Int. Cl.
*G06Q 50/00* (2012.01)
*A61C 1/08* (2006.01)
*A61C 13/00* (2006.01)
*G06Q 10/00* (2012.01)

(52) U.S. Cl.
CPC ............ *A61C 1/084* (2013.01); *A61C 13/0004* (2013.01)

(58) Field of Classification Search
USPC ............................................................ 705/2
See application file for complete search history.

(56) References Cited

U.S. PATENT DOCUMENTS

| | | | |
|---|---|---|---|
| 4,796,181 A * | 1/1989 | Wiedemer | 705/52 |
| 5,224,049 A | 6/1993 | Mushabac | |
| 5,368,478 A | 11/1994 | Andreiko et al. | |
| 5,452,407 A * | 9/1995 | Crook | 345/421 |
| 5,453,009 A | 9/1995 | Feldman | |
| 5,556,278 A * | 9/1996 | Meitner | 433/75 |
| 5,740,800 A | 4/1998 | Hendrickson et al. | |
| 5,930,759 A | 7/1999 | Moore et al. | |
| 6,032,119 A | 2/2000 | Brown et al. | |
| 6,199,115 B1 | 3/2001 | DiRienzo | |
| 6,264,614 B1 * | 7/2001 | Albert et al. | 600/528 |
| 6,287,119 B1 | 9/2001 | van Nifterick et al. | |
| 6,582,225 B1 | 6/2003 | Bergersen | |
| 6,786,726 B2 * | 9/2004 | Lehmann et al. | 433/223 |
| 6,821,123 B2 | 11/2004 | Andersson et al. | |
| 7,089,070 B1 | 8/2006 | Andersson et al. | |
| 2005/0130104 A1 * | 6/2005 | Robichaud et al. | 433/173 |

OTHER PUBLICATIONS

Dario, Smart surgical tools and augmenting devices,[.IEEE Trans. Robot. Automat., vol. 19, No. 5, pp. 782-792, Oct. 2003.*
Van der Zel JM, Bites for the Computer, ISBN 9056293591, Vossiuspers, University of Amsterdam, Amsterdam, 2004.*

* cited by examiner

*Primary Examiner* — Ken Nguyen

(57) ABSTRACT

An improved system and method for the design, creation and installation of implant-supported dental prostheses is provided. A network accessible portal facilitates communication among a dental professional, a scanning center, a manufacturing center and others in the design and production of a dental drill guide and prosthesis, utilizing cone beam imaging, a rotatable 3-dimension representation of a patient's jaw, virtual placement of one or more implants and virtual testing prior to manufacture. Dental professionals may access the portal on a subscription or non-subscription basis.

15 Claims, 51 Drawing Sheets

SYSTEM AND METHOD FOR THE DESIGN, CREATION AND INSTALLATION OF IMPLANT-SUPPORTED DENTAL PROSTHESES

Claim is hereby made for the benefit of U.S. Provisional Application No. 60/738,516 filed Nov. 22, 2005, and U.S. Provisional Application No. 60/828,064, filed Oct. 3, 2006, incorporated herein in their entirety by reference.

FIELD OF THE INVENTION

The present invention relates to the field of systems & methods for the design, creation and installation of implant-supported dental prosthesis.

BACKGROUND OF THE INVENTION

It is well known in the art that some dental patients require restoration of teeth. In particular, there are some patients whose teeth are no longer present, or whose teeth have deteriorated to the degree that they cannot serve as a platform for the mounting of traditional dental prosthetics, e.g. bridges.

Implants, now in use for about forty years, are the standard way to attach fixed dental prostheses in place. One implant may support a single replacement tooth, usually cemented atop an abutment. Where several teeth are missing, two or more implants may be used.

In traditional implant-supported prosthesis installation, implants are first installed by an oral surgeon. He or she first examines the areas in which implants are needed, refers to conventional dental x-rays to learn if the underlying bone structure appears suitable to support implants. This information is, however, not fully revealed by conventional two-dimensional x-ray images. If bone structure is not adequate, additional surgery may be needed to enhance it. After any required bone enhancement, based on x-rays and personal judgment, the surgeon drills a cavity for each implant, using a manually held drill. Each implant is then screwed into place with a wrench. In most instances, the patient's dentist would carry out the remaining steps.

Unaided manual preparation of a jaw for implants is challenging, especially if done infrequently by a practitioner, because of the difficulty in estimating positions and angles accurately by eye, within a deep hole of small diameter in a patient's mouth. Even if the work is being done by an experienced dentist or oral surgeon, chances for location or orientation errors are great. By analogy with woodworking practice, some form of drill guide should be of considerable help in preparing implant cavities. Because of the necessary complexity of a guide adjustable to any patient and case, a guide customized for the patient and case is preferable.

One way to create a custom implant drill guide involves use of Cone Beam technology to capture an enhanced view of the upper and lower jaw region of a patient's head. The resulting imagery can show the bone structure and teeth in detail as well as the soft tissues. Using specially designed software that aids in predefining appropriate implant locations, the Cone Beam data can be used to create another set of data defining the location, orientation, and depth of each cavity to be prepared. From this, with use of a numerically controlled drilling tool, a patient- and case-customized drill guide is constructed. When properly mounted in the patient's mouth, guide holes in this unit align the drilling tool for its use in creating each predefined implant cavity. Each implant is then inserted and moved into its permanent location.

After installation of implants, traditional procedure varies, depending on how long a delay (of up to six months) is allowed for accommodation of the implant(s) by the bone of the jaw (osseointegration). Some implant manufacturers recommend loading implants immediately, others do not. If a healing delay is to be observed, a healing abutment—a metal extension washer with a domelike-top—is fastened to each implant by a screw in the threaded hole of the implant, and the gum flesh is sutured over the abutment.

On successful completion of the implant procedure, the patient returns to his Dentist for the later process steps. To install the prosthesis, tissue over the implants is reopened using a knife or a punch. The healing abutments are removed from the implants to reveal the surfaces on which the frame's attachment points will rest. Dental impressions are made of upper and lower jaws. Molds (positive models of the jaws) are made from these impressions, in a traditional procedure. The physical molds after being shipped to a dental laboratory are used to build up a prosthesis, in a traditional highly labor-intensive process demanding high skill level and long experience for good results.

The established paradigm for prosthesis construction, save for very small prostheses, involves constructing initially a rigid (therefore, heavy) metal structure which we shall refer to as the frame or framework. (Some sources refer to it as a bar.) It incorporates one short, hollow cylindrical attachment element for each implant. The attachment cylinders are connected using simple shapes. All is first modeled using hand-assembled solid and liquid plastics then cast in a suitable metal or alloy. After casting, if adjustment is required, it is customarily done using manual tools. Each attachment cylinder is positioned and oriented to fit snugly atop its corresponding implant and to accept a screw holding it to the implant. With these screws in place in all implants, the frame will be rigidly attached to the jaw. Since the attachments on the frame extend somewhat beyond the frame itself, when the frame is attached to the implants it stands slightly above the gum. This space is later filled with molded thermoplastic resin closely fitting the contour of the jaw.

After the frame is created, it is mounted to the model of the patient's corresponding jaw made by his or her dentist. Both models are then articulated on a conventional hinged metal mounting. A suitable type and size of artificial tooth for each replacement location is selected from a graded set of pre-molded teeth of each type (molar, bicuspid, etc.). The closed-mouth spacing between upper and lower jaw teeth is verified using the measurements made before restoration work was begun.

The remainder of the traditional prosthesis construction consists of firmly locating artificial teeth and fastening them in place, shaping thermoplastic resin smoothly over the outside of the frame and the gums, and preparing the clearance holes for the attachment screws.

Installation, as in most corrective dentistry, may require removal of small amounts of material from the prosthesis in places where it is tight ("milling-in"). If the implant-to-prosthesis connecting surfaces do not match exactly, within limits some grinding or filing can be done, as is also true for traditional prostheses. After the prosthesis has been fitted, the screw access holes needed to fasten prosthesis to implants will be filled with plastic resin and smoothed.

One group of limitations of prior-art procedures are those associated with unaided manual preparation of the mouth for, and placement of, dental implants:

a) The human jawbone is highly variable in thickness from location to location, and varies from person to person.

Thus, for a given individual's jaw, certain implant locations are preferable to others because of bone strength variations.

b) For implant attachment strength, the optimal direction at which the implant should pass into the bone varies from one jaw location to another, and bone configurations are different from person to person. If the hole in the bone is drilled at an incorrect location and/or angle, the tip of the implant may pass through the bone and out the far side, weakening its attachment strength. Protruding implant tips also raise patient objections on cosmetic grounds.

c) Poor placement of implants can be a source of problems in installing and using a prosthesis. If implants exit the jaw out-of-parallel with one another it will be more difficult to align the prosthesis to the implants. In addition, when implant axes are far from parallel, biting forces will translate from purely compressive force to bending force more likely to fracture the bone.

d) Even if conventional x-ray images or computer tomographic (CT) scan images are available for a patient's jaw, a practitioner preparing a jaw for implants without some form of drilling guide must make on-the-spot decisions as to location, must estimate angles without visual help and in an irregularly shaped environment (the mouth), needs exceptional hand-eye coordination (even for a dentist), and must make exacting position estimates unaided.

Additional problems and limitations occur during design and construction of prostheses:

a) They are the most labor-intensive products used in dental practice, and require expensive metals and plastics. In traditional design the prosthesis frame is often heavy, since it may be modeled manually by fastening simple plastic shapes together with liquid plastic filler.

b) Fully trained and experienced technicians skilled in this work do not emerge from vocational schools and colleges. Most dental laboratories lack large enough and capable enough staffs to teach the full range of needed skills to each new employee. In short, automation of critical parts of the work is much needed.

c) Traditional prosthesis construction techniques employ materials that often must be chosen for ease in use during the largely manual construction process, rather than for their properties in the final product. Use of a heavy, rigid frame for prostheses is probably not optimal in the oral environment, where bones are brittle, teeth are hard and tough, but adjacent ligament and gum tissue are elastic and softer.

d) Certain difficulties and diseconomies occur because of the complexity of the process of acquiring and installing a quality prosthetic, variations from case to case reflected in the assembly process, and the ad hoc nature of the work.

Traditionally, a large proportion of communications between a dentist and others involved in restoration have been through physical transmission of bulky impressions or models of patients' jaws. Close proximity of dentists to supporting laboratory organizations has traditionally been desirable. New broadband communication technologies based on the Internet have enabled different ways of operating.

Other problems exist.

Related art includes the following patents:

U.S. Pat. No. 5,224,049, issued to Mushabac on Jun. 29, 1993

U.S. Pat. No. 5,368,478, issued to Andreiko et al. on Nov. 29, 1994

U.S. Pat. No. 5,453,009, issued to Feldman on Sep. 26, 1995

U.S. Pat. No. 5,740,800, issued to Hendrickson et al. on Apr. 21, 1998

U.S. Pat. No. 5,930,759, issued to Moore, et al. on Jul. 27, 1999

U.S. Pat. No. 6,032,119, issued to Brown et al. on Feb. 29, 2000

U.S. Pat. No. 6,199,115, issued to DiRienzo on Mar. 6, 2001

U.S. Pat. No. 6,287,119, issued to van Nifterick et al. on Sep. 11, 2001

U.S. Pat. No. 6,582,225, issued to Bergersen on Jun. 24, 2003

U.S. Pat. No. 6,786,726, issued to Lehmann et al. on Sep. 7, 2004

U.S. Pat. No. 6,821,123, issued to Andersson et al. on Nov. 23, 2004

U.S. Pat. No. 7,089,070, issued to Andersson et al. on Aug. 8, 2006

While these patents and other previous methods have attempted to solve the problems that they addressed, none have utilized or disclosed an improved system and method for the design, creation and installation of implant-supported dental prostheses, as does embodiments of the present invention.

Therefore, a need exists for an improved system and method for the design, creation and installation of implant-supported dental prostheses with these attributes and functionalities. The improved system and method for the design, creation and installation of implant-supported dental prostheses according to embodiments of the invention substantially departs from the conventional concepts and designs of the prior art. It can be appreciated that there exists a continuing need for a new and improved an improved system and method for the design, creation and installation of implant-supported dental prostheses which can be used commercially. In this regard, the present invention substantially fulfills these objectives.

The foregoing patent and other information reflect the state of the art of which the inventors are aware and are tendered with a view toward discharging the inventor's acknowledged duty of candor in disclosing information that may be pertinent to the patentability of the present invention. It is respectfully stipulated, however, that the foregoing patent and other information do not teach or render obvious, singly or when considered in combination, the inventor's claimed invention.

BRIEF SUMMARY OF THE INVENTION

The general purpose of the present invention, which will be described subsequently in greater detail, is to provide an improved system and method for the design, creation and installation of implant-supported dental prostheses.

Generally speaking, the present invention is directed to a highly systematic process for diagnosis, specification, construction and installation of prostheses supported by dental implants. The process is primarily automated and employs current and future non-ionizing scanning and imaging, e.g. Cone Beam, Electron Imaging, digital imagery and data-conversion techniques to reduce both labor and total time required for diagnosis, creation, and installation of implant-supported dental prostheses. The present invention is directed to the elimination of much of the highly skilled, precise hand work by dental professionals and prosthesis technicians that was required by prior-art procedures.

Prostheses produced by this process are of the fixed type, i.e., not intended for insertion or removal by the patient.

In general terms the present invention is directed to the creation of a digital model of the mouth (upper jaw, lower jaw) distinctly illustrating gum, teeth, and bone structure so that implant location can be determined and a drill guide and prosthesis may be designed and manufactured.

The process is directed primarily to dentists who are not oral surgeons.

The process is directed to location agnostic interaction, i.e. the ability to have convenient interactivity.

The process is directed to the creation of a 1-tooth prosthesis, a 2-4 teeth prosthesis or a 4-16 teeth prosthesis.

One aspect of the present invention is it replaces physical shipment with transmission of electronic data representing patients' jaws. Most of this data will be in the form of density data captured by cone beam scanning devices, and the like. Part of the teaching in this specification is about how to use that type of data for design and construction of dental prosthetics.

Another aspect of the present invention is that it removes much of the uncertainty of the position and angle for placement of implant holes by automating the process of determining implant placement. The combination of high-resolution 3-D imagery, computer-based planning of implant locations, and a patient-unique drill guide moves implant installation into a zone of reasonable-risk.

Another aspect of the present invention is the availability of a Portal giving access to information and one-on-one professional on-line guidance from experienced professionals. Use of the Portal for scheduling and other routine office activities will ensure that it is familiar to the professional and his or her staff.

Another aspect of the present invention is that precision placement of implants by this process means that the patient's biting or chewing loads may be better distributed across the jaw than if implants were haphazardly located.

Another aspect of the present invention is the use of pattern recognition in the process of creating a drill guide.

Another aspect of the present invention is that it enables dentists to earn additional income.

Another aspect of the present invention is that it provides more informative and precise 3D imaging.

Another aspect of the present invention is that it provides faster delivery of implant services to a patient.

Another aspect of the present invention is that it provides 24×7×365 customer support.

Another aspect of the present invention is that nominal training is required.

Another aspect of the present invention is that a prosthetic is created based on the exact model of patent jaw.

Another aspect of the present invention is that a dentist is able to view his patient data from any location having internet access and consult with a specialist who has access to the same data.

These and other features and advantages of the present invention will be presented in more detail in the following specification of the invention and the accompanying figures, which illustrate by way of example the principles of the invention.

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE SEVERAL VIEWS OF THE DRAWINGS

The invention, together with further advantages thereof, may best be understood by reference to the following description taken in conjunction with the accompanying drawings in which:

FIG. 39 illustrates an image data storage web page for an improved system and method for the design, creation and installation of implant-supported dental prostheses according to one embodiment of the present invention.

FIG. 42 illustrates a storage of reconstructed image data for an admin team web page for an improved system and method for the design, creation and installation of implant-supported dental prostheses according to one embodiment of the present invention.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

Figure 1:
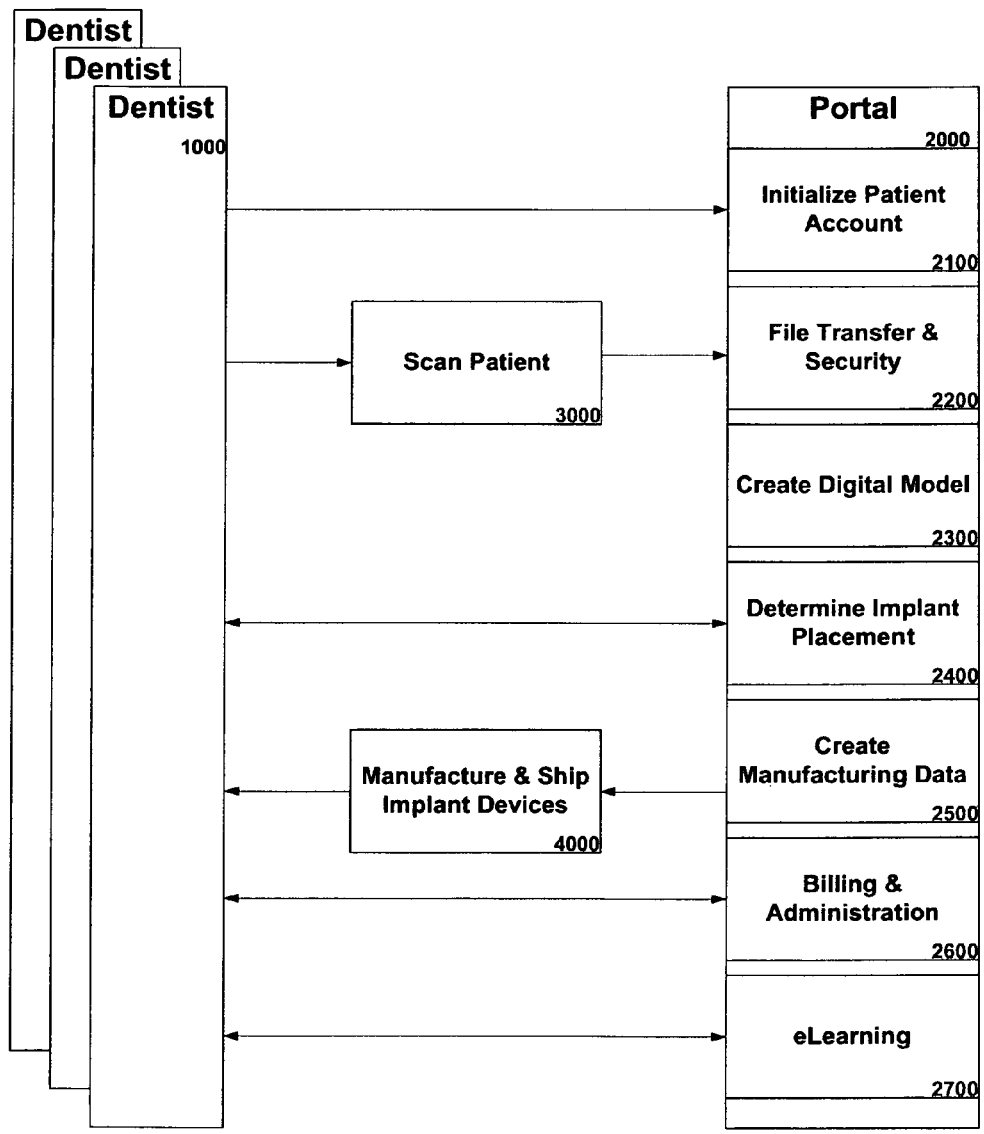
FIG. 1 is a flow diagram illustrating an process overview of an improved system and method for the design, creation and installation of implant-supported dental prostheses according to one embodiment of the present invention.

Referring now to FIG. 1, the relationship between a portal 2000 and a dentist 1000 is illustrated for an embodiment of the present invention. A dentist 1000 refers a patient to a scanning center after diagnosing and recommending an implant procedure. An initialize patient account 2100 module is used by the dentist to establish a secure account for the patient. At the scan patient 3000 portion of the process, Cone Beam technology is used to create digital data of the bone, teeth and gum. This data is received at the portal and placed into the patient's account using the file transfer & security 2200 module. A create digital model 2300 module uploads the data and creates a rotatable 3D image showing the bone structure, teeth, gums and palate of the patient. This image is used in a determine implant placement 2400 module to determine optimum and alternative placement for one or more implants. Once the dentist confirms the implant placement, data is sent to a create manufacturing data 2500 module where a drill guide and a frame are designed and tested virtually. The manufacturing data is transmitted to a manufacturing facility where the devices are made and shipped to the dentist for use in the implant procedure. A billing & administration 2600 module bills the dentist and maintains administrative data. An eLearning module is available for orientation and instruction of a dentist.

Figure 2:
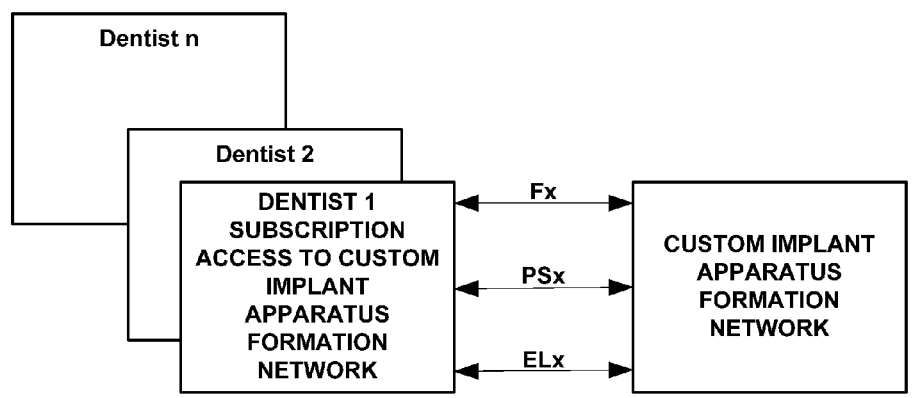
FIG. 2 is a flow diagram of an improved system and method for the design, creation and installation of implant-supported dental prostheses illustrating elements for subscription access according to one embodiment of the present invention.

FIG. 2 illustrates three aspects of an improved system and method for the design, creation and installation of implant-supported dental prostheses for dentists accessing an embodiment of the system on a subscription basis. Fx represents the financial elements. PSx represents the product and services elements. ELx represents the e-learning elements.

Figure 3:
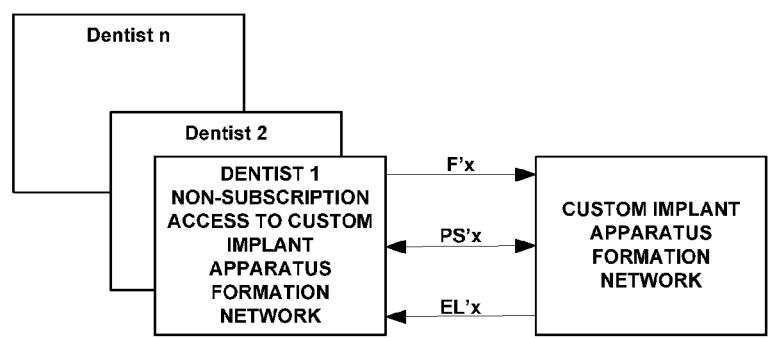
FIG. 3 is a flow diagram of an improved system and method for the design, creation and installation of implant-supported dental prostheses illustrating elements for non-subscription access according to one embodiment of the present invention.

FIG. 3 illustrates three aspects of an improved system and method for the design, creation and installation of implant-supported dental prostheses for dentists accessing an embodiment of the system on a non-subscription basis. F'x represents the financial elements. PS'x represents the product and services elements. EL'x represents the e-learning elements.

Figure 4:
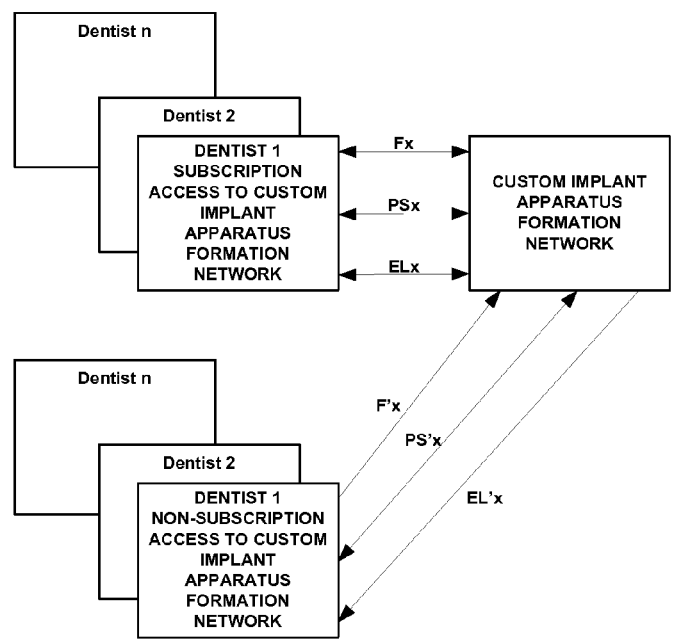
FIG. 4 is a flow diagram of an improved system and method for the design, creation and installation of implant-supported dental prostheses illustrating elements for both subscription and non-subscription access according to one embodiment of the present invention.

FIG. 4 illustrates a combined model where both subscription and non-subscription dentists are participating.

Figure 5:
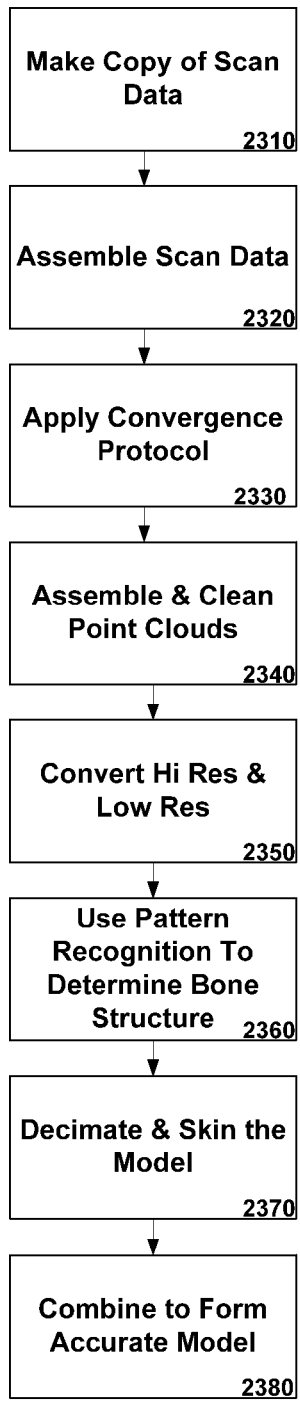
FIG. 5 is a flow diagram giving further detail of the elements in the create digital model module.

FIG. 5 is a flow diagram giving further detail of the elements in the create digital model 2300 module. Elements of this module include make copy of scan data 2310, assemble scan data 2320, apply convergence protocol 2330, assemble & clean point clouds 2340, convert high resolution and low resolution 2350, use pattern recognition to determine bone structure 2360, decimate & skin the model 2370 and combine to form accurate model 2380.

Figure 6:
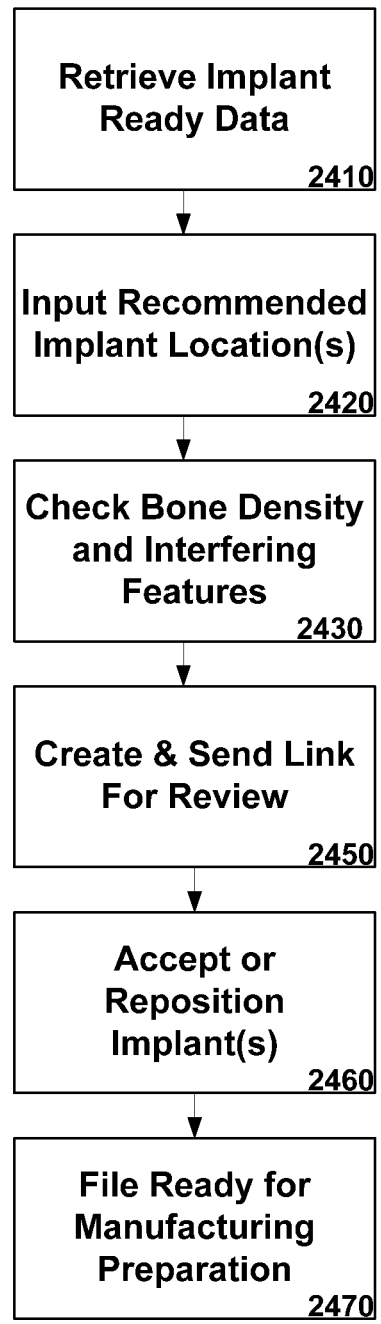
FIG. 6 is a flow diagram giving further detail of the elements in the determine implant placement module.

FIG. 6 is a flow diagram giving further detail of the elements in the determine implant placement 2400 module. Elements of this module include retrieve implant ready data 2410, input recommended implant location(s) 2420, check bone density and interfering features 2430, create & send link for review 2450, accept or reposition implant(s) 2450 and file ready for manufacturing preparation 2470.

Figure 7:
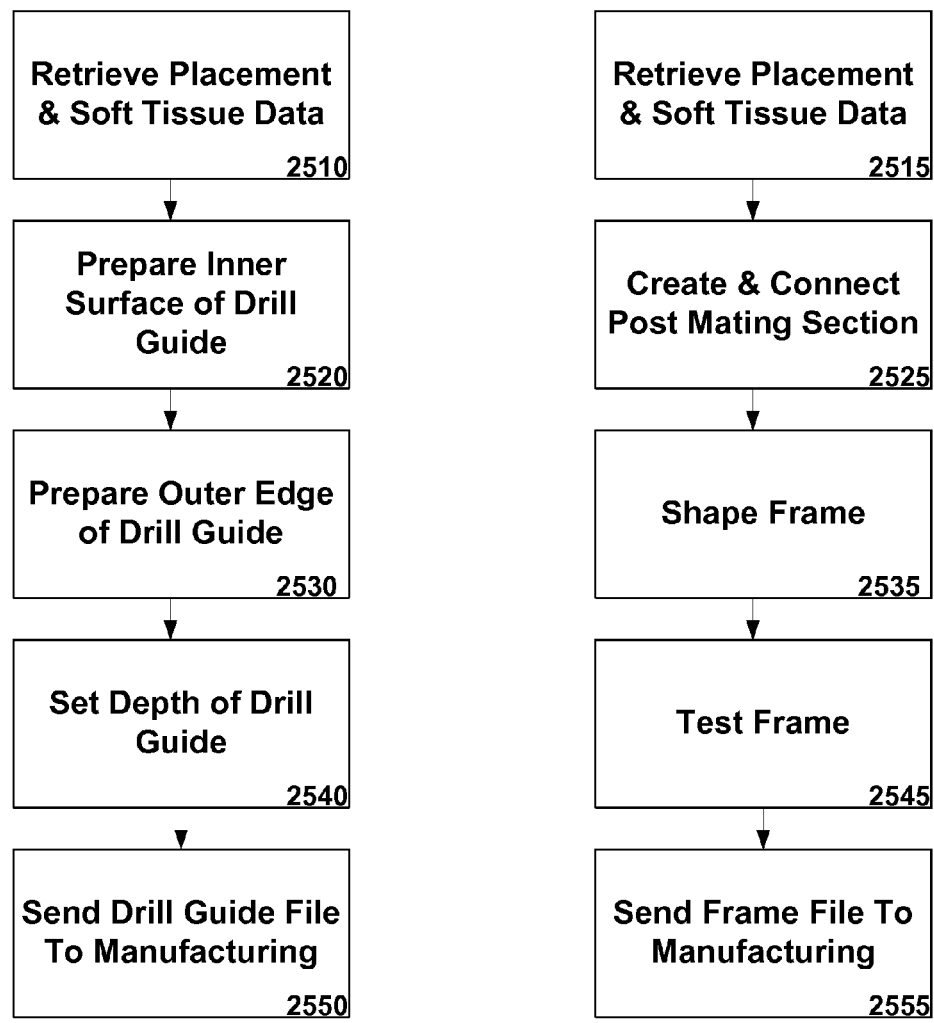
FIG. 7 is a flow diagram giving further detail of the elements in the create manufacturing data module.
Figure 8:
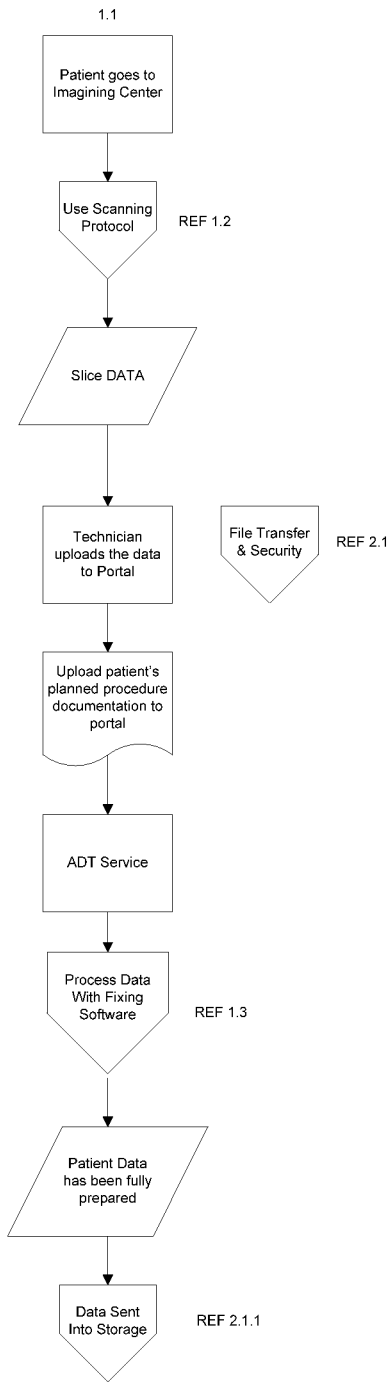
FIG. 8 is a flow diagram illustrating a partial overview of one embodiment of the present invention.
Figure 9:
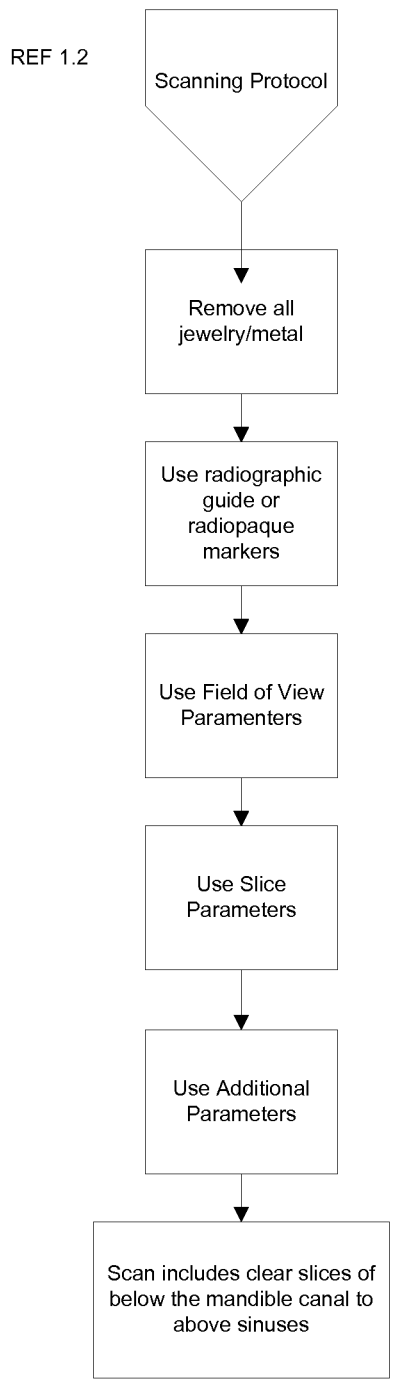
FIG. 9 is a flow diagram illustrating scanning protocol in one embodiment of the present invention.
Figure 10:
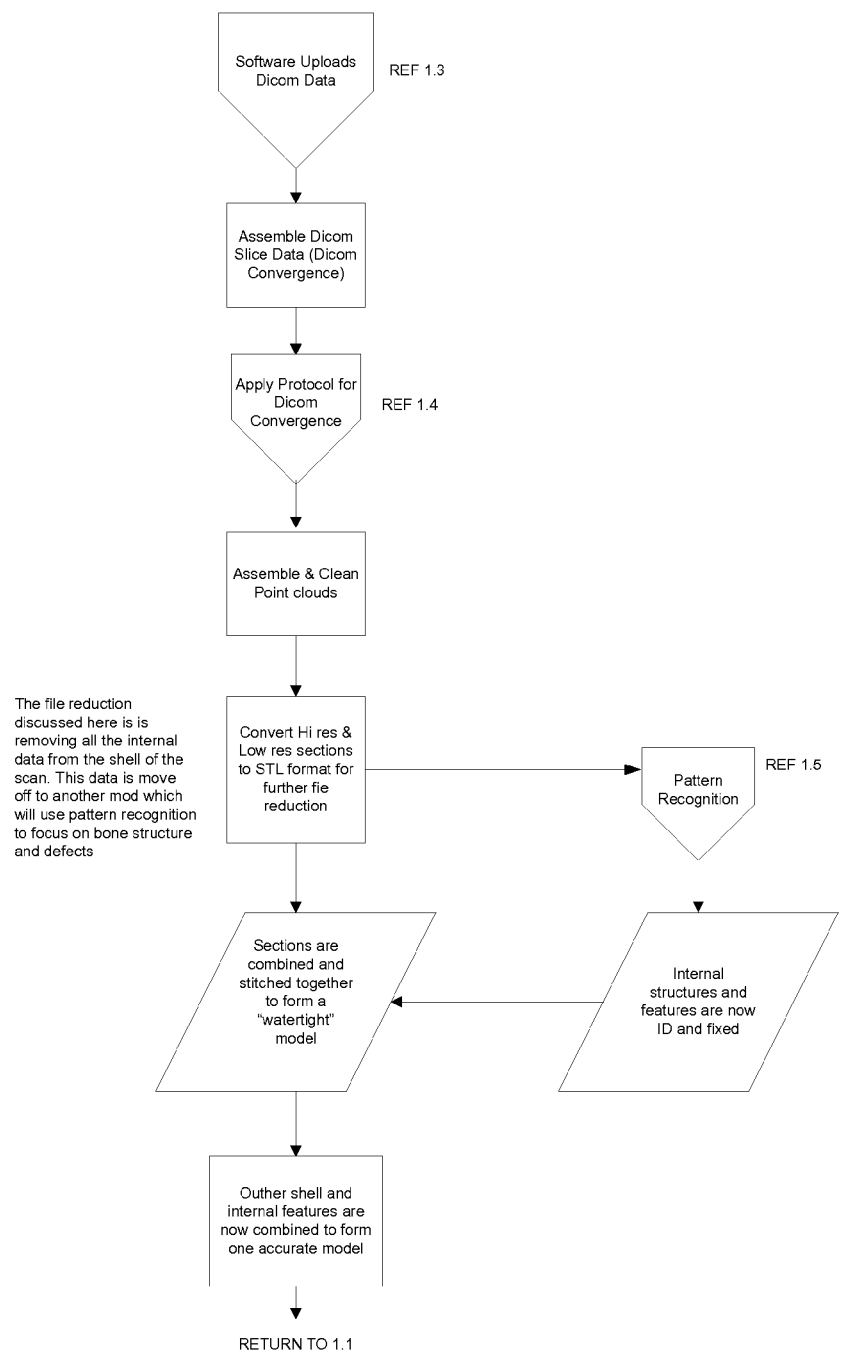
FIG. 10 is a flow diagram illustrating a Fixing Data module in one embodiment of the present invention.
Figure 11:
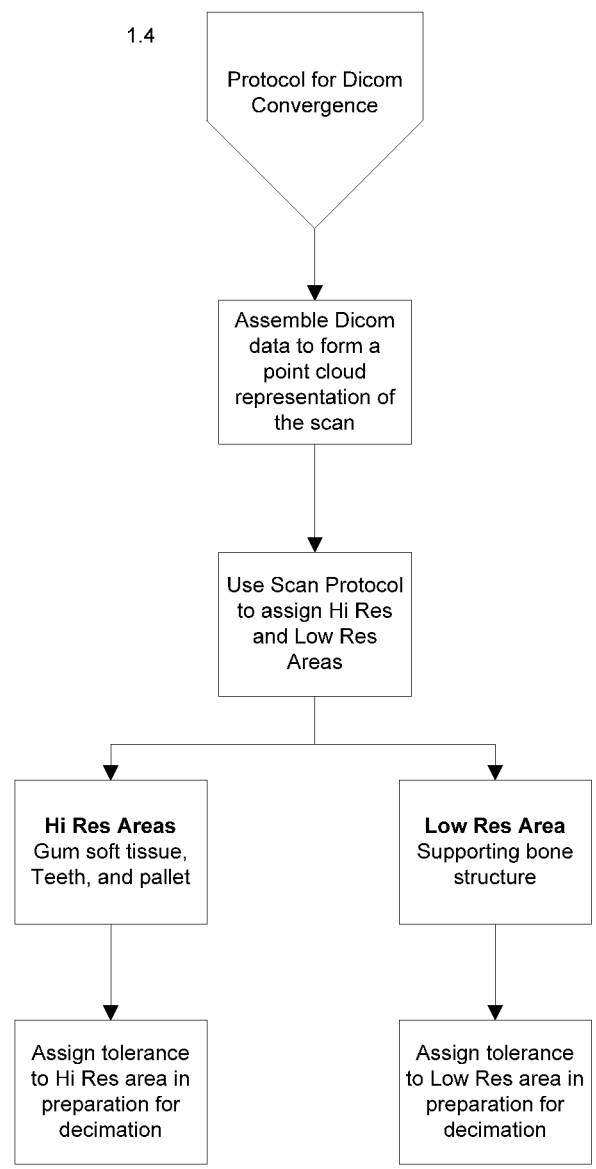
FIG. 11 is a flow diagram illustrating a Protocol for Dicom Convergence module in one embodiment of the present invention.
Figure 12:
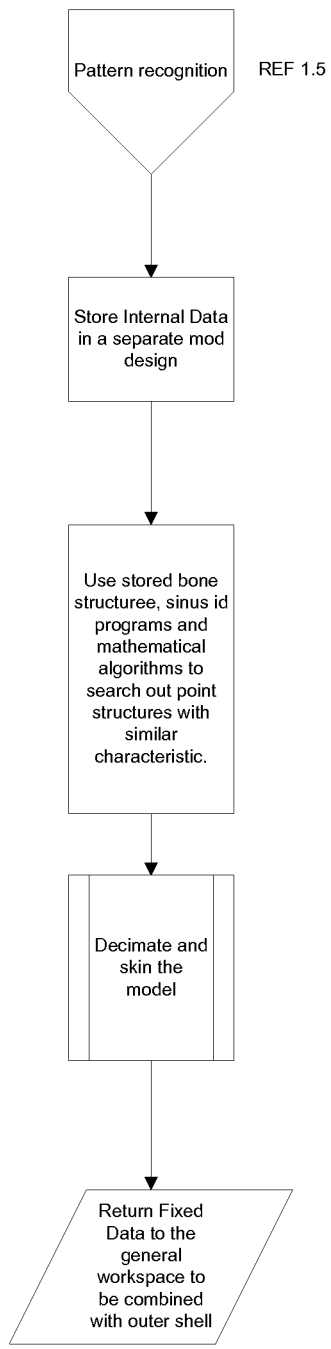
FIG. 12 is a flow diagram illustrating a Pattern Recognition module in one embodiment of the present invention.
Figure 13:
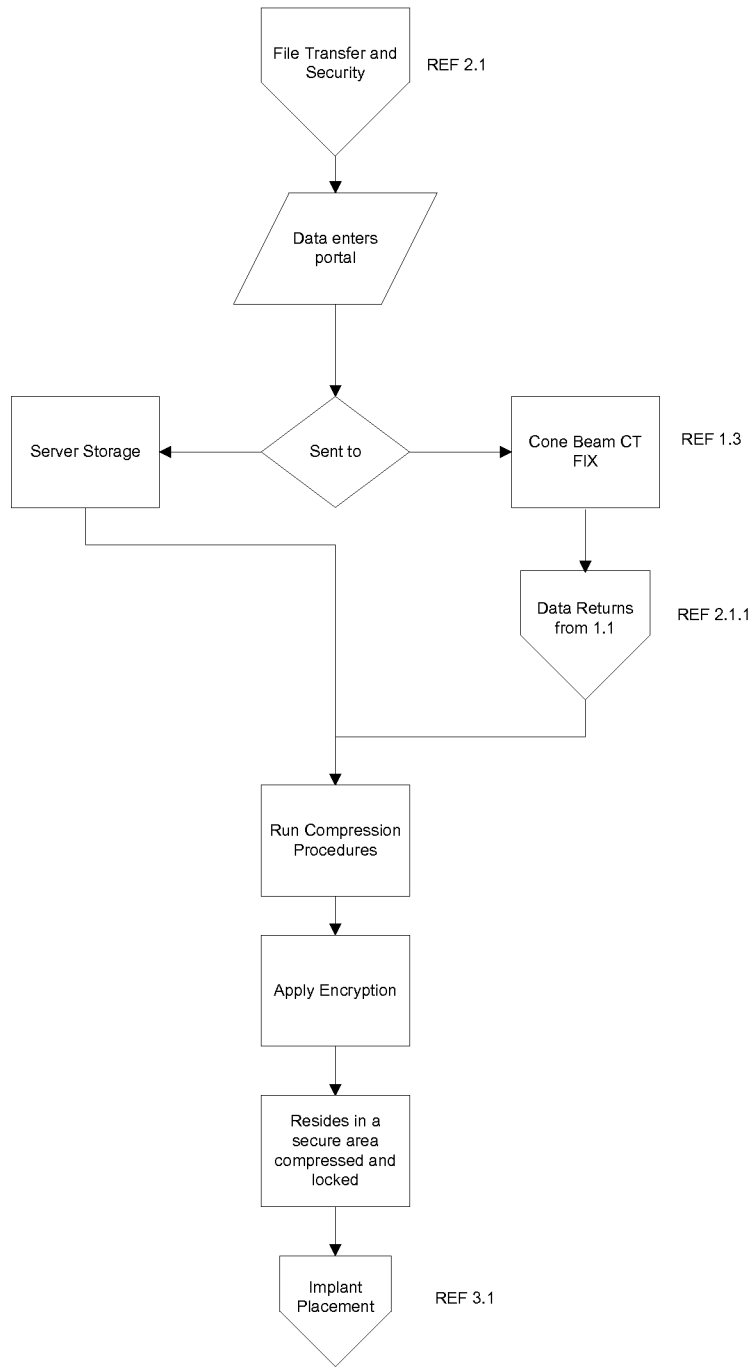
FIG. 13 is a flow diagram illustrating a partial overview of one embodiment of the present invention.
Figure 14:
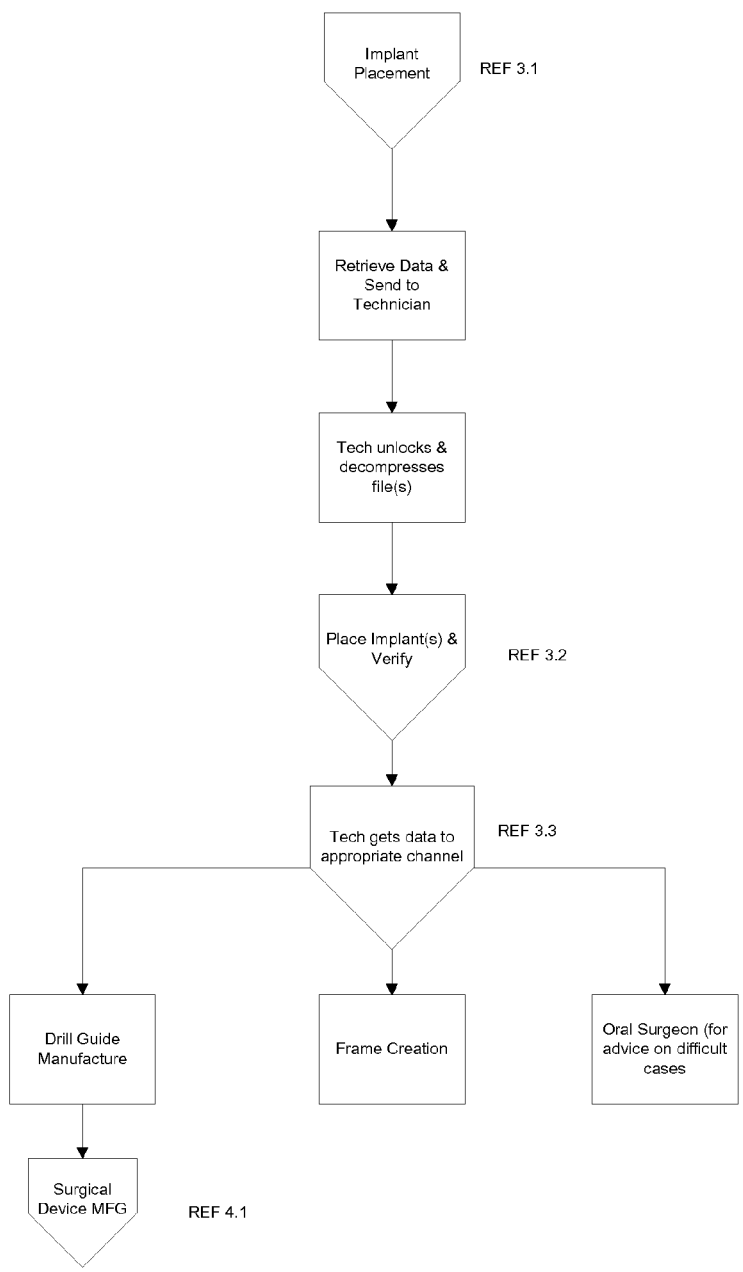
FIG. 14 is a flow diagram illustrating an Implant Placement module in one embodiment of the present invention.
Figure 15:
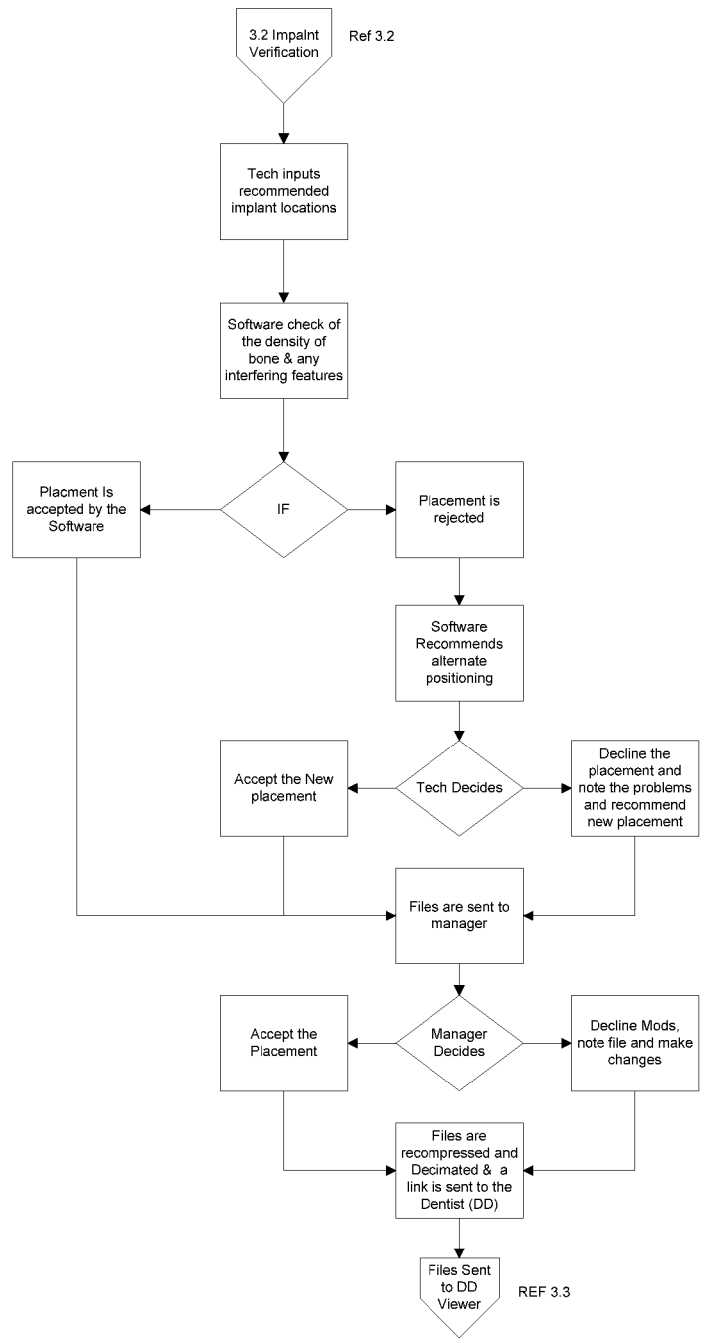
FIG. 15 is a flow diagram illustrating an Implant Verification module in one embodiment of the present invention.
Figure 16:
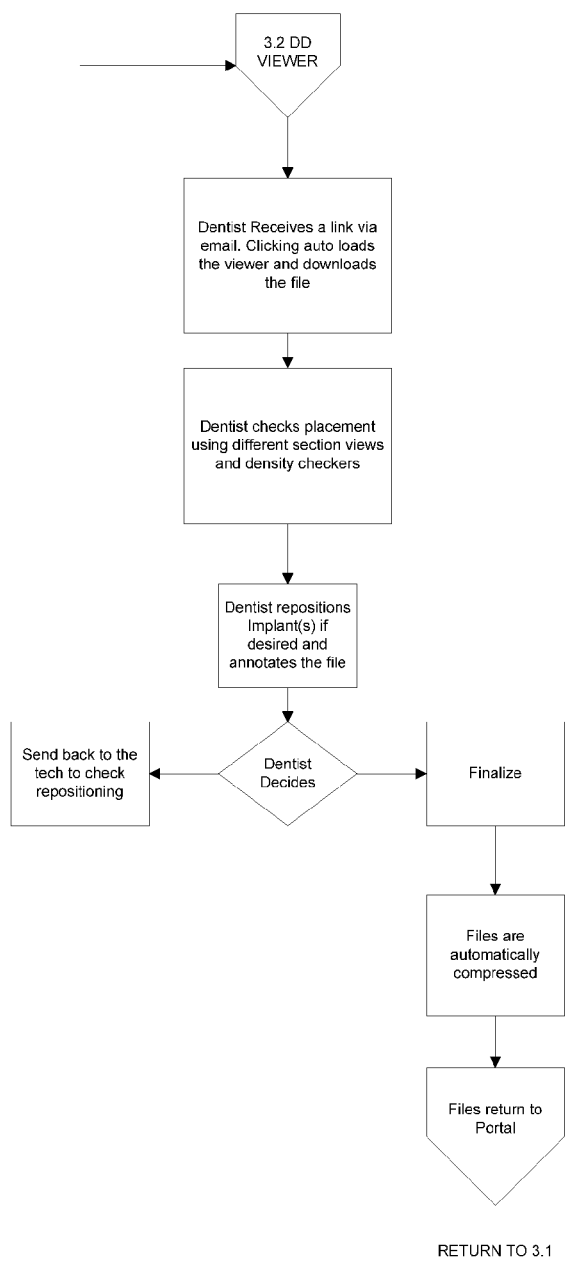
FIG. 16 is a flow diagram illustrating a Dentist Viewer module in one embodiment of the present invention.
Figure 17:
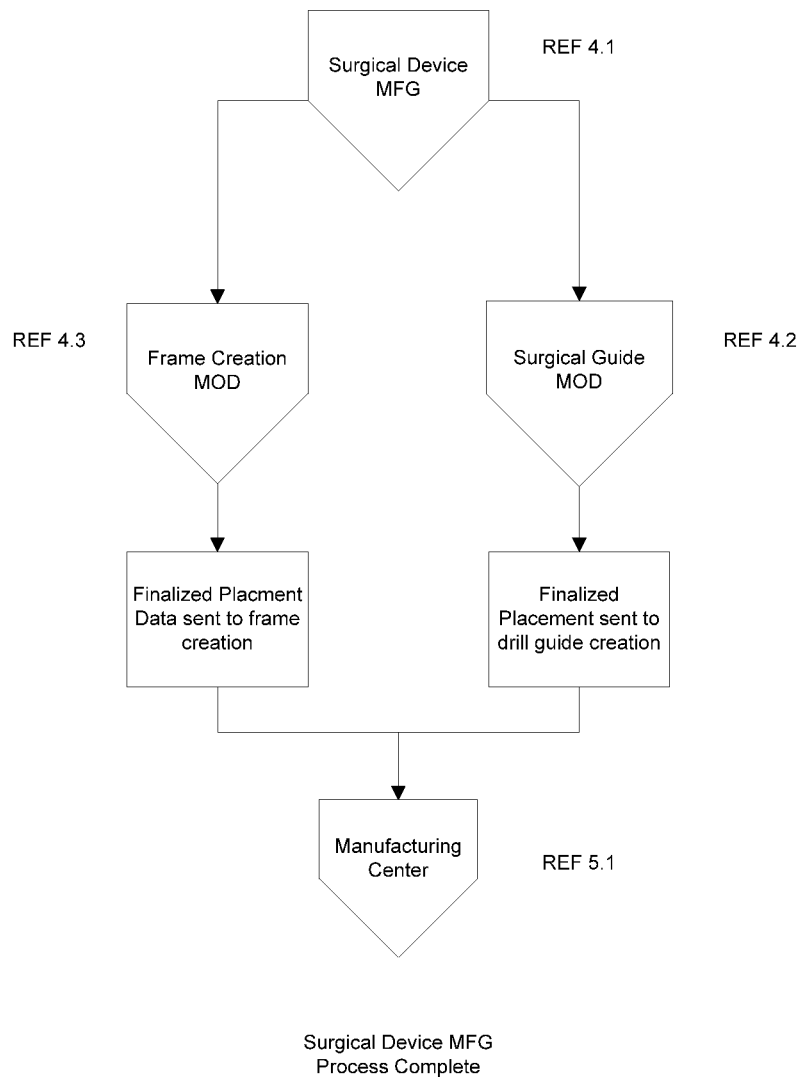
FIG. 17 is a flow diagram illustrating an overview of the surgical manufacturing process in one embodiment of the present invention.
Figure 18:
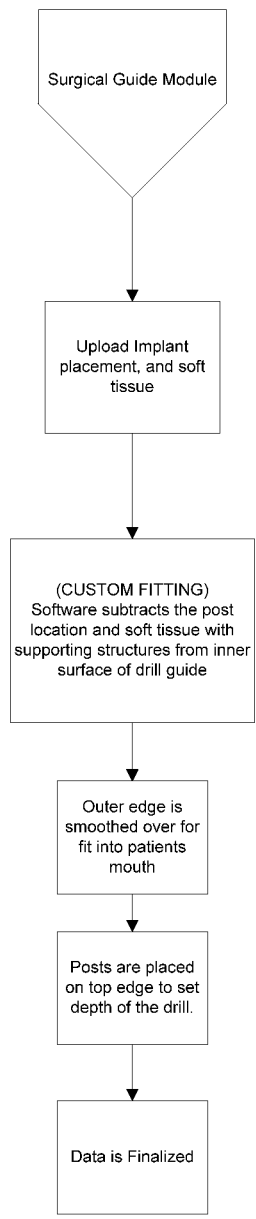
FIG. 18 is a flow diagram illustrating a Surgical Guide Creation module in one embodiment of the present invention.
Figure 19:
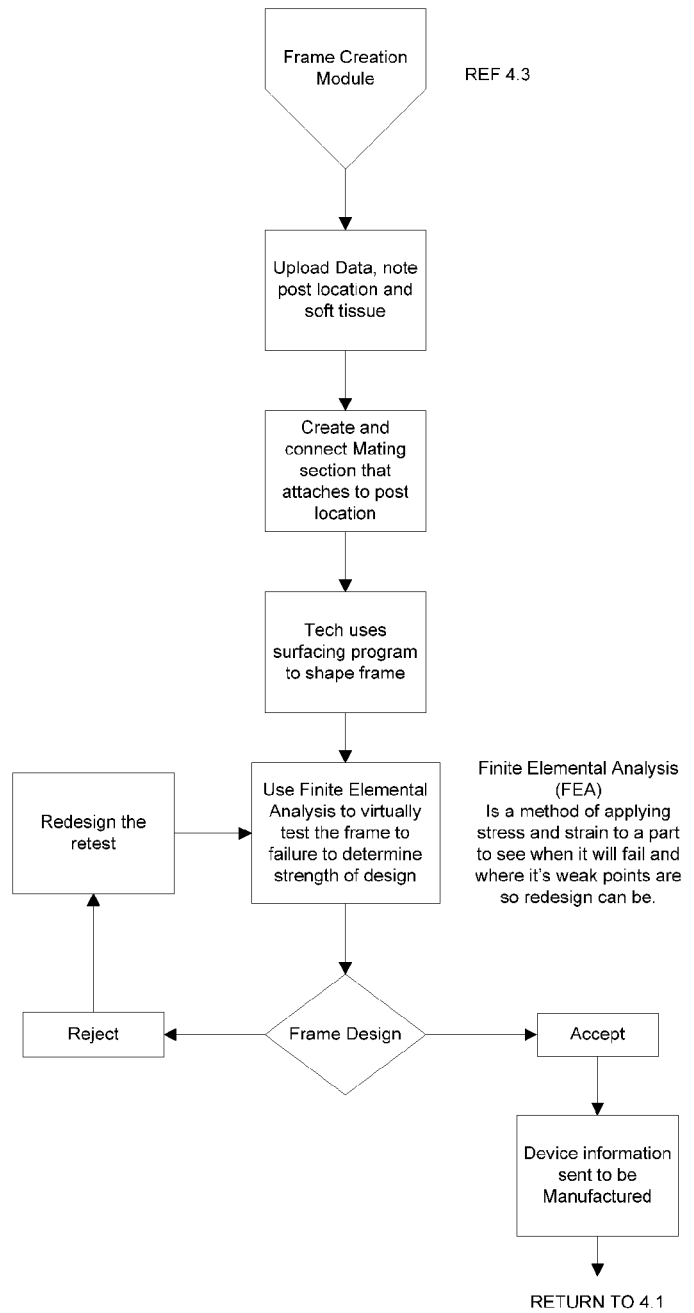
FIG. 19 is a flow diagram illustrating a Frame Creation module in one embodiment of the present invention.
Figure 20:
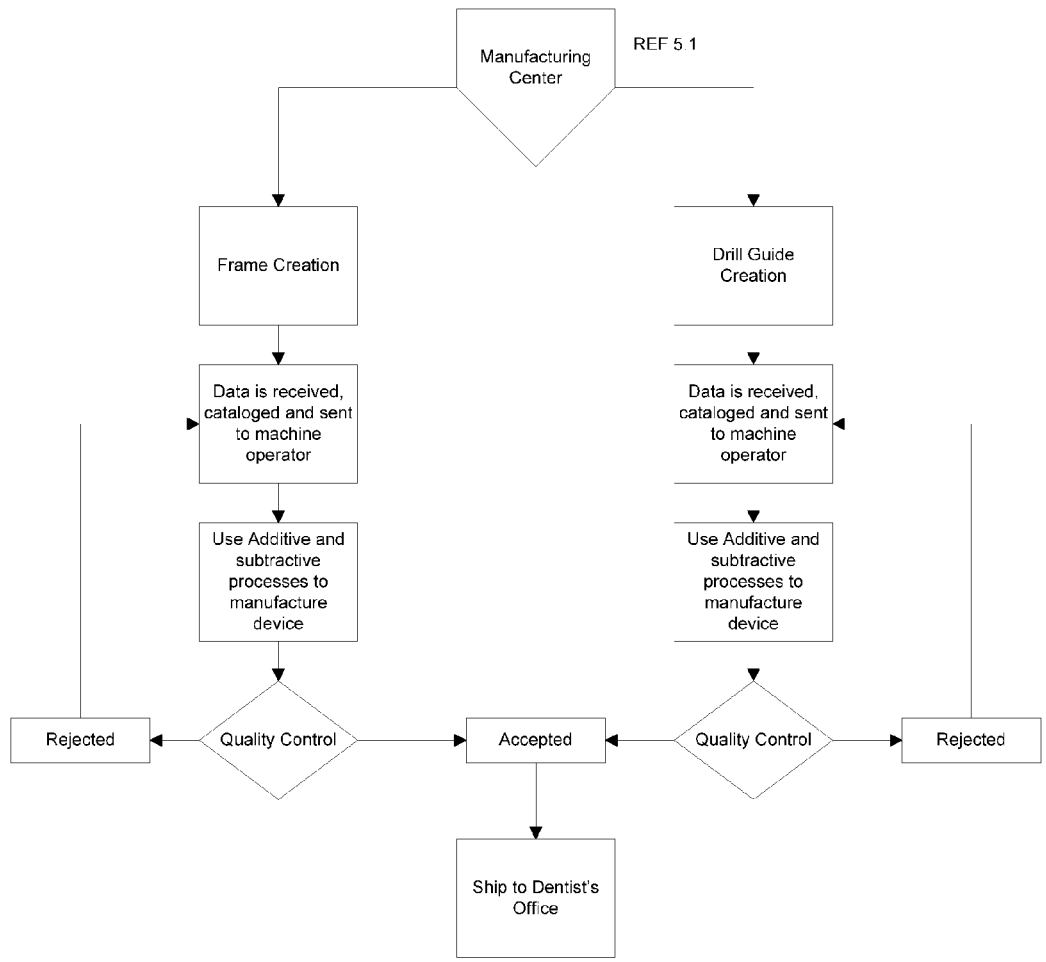
FIG. 20 is a flow diagram illustrating a Manufacturing Center process in one embodiment of the present invention.

FIG. 7 is a flow diagram giving further detail of the elements in the create manufacturing data module. Parallel paths are shown for the drill guide design and the frame design. Elements of this module include retrieve placement & soft tissue data 2510, prepare inner surface of drill guide 2520, prepare outer edge of drill guide 2530, send drill guide file to manufacturing 2550, retrieve placement & soft tissue data 2515, create & connect post mating section 2525, shape frame 2535, test frame 2545, and sent frame file to manufacturing 2555.

FIG. 8 through FIG. 20 illustrate processes for an embodiment of the present invention.

Figure 21:
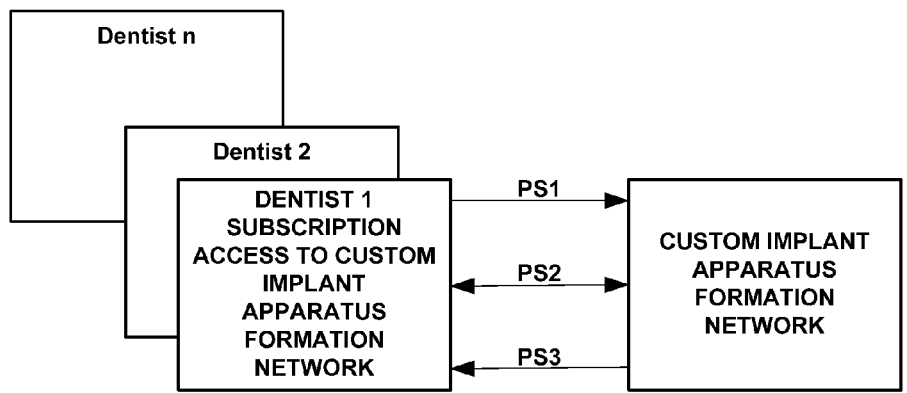
FIG. 21 is a flow diagram of a subscription access product and services process for an improved system and method for the design, creation and installation of implant-supported dental prostheses according to one embodiment of the present invention.

FIG. 21 illustrates three aspects of the product and services elements. PS1 represents an imaging service for a referred patient. PS2 represents the services in processing that image to the point that a drill guide is authorized. PS3 represents the manufacture and delivery of a drill guide kit to a dentist.

Figure 22:
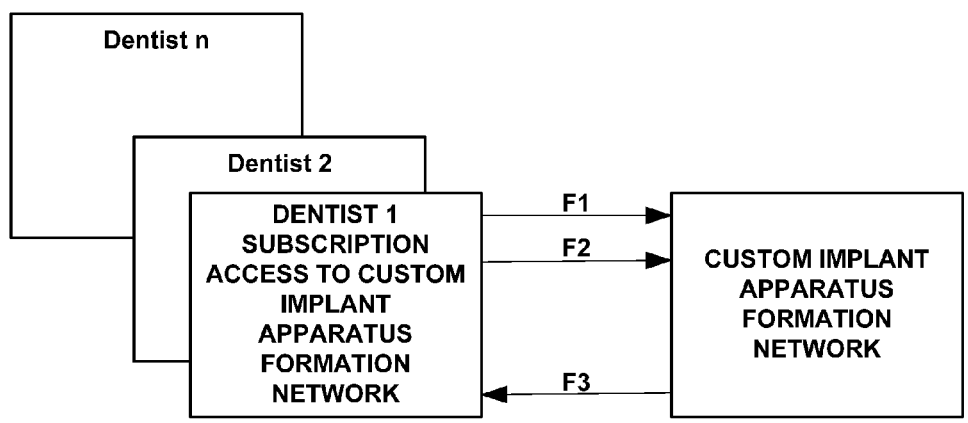
FIG. 22 is a flow diagram of a subscription access financial process for an improved system and method for the design, creation and installation of implant-supported dental prostheses according to one embodiment of the present invention.

FIG. 22 illustrates three aspects of the financial elements for a dentist subscriber. F1 represents a dentist's financial investment in the system in order to access the system on a subscription basis. F2 represents a payment by a dentist for a product and/or a service provided by the system. F3 represents a payout, e.g. a dividend, to a subscribing member. Financial flows to vendors, employees, experts and founders are not shown.

Figure 23:
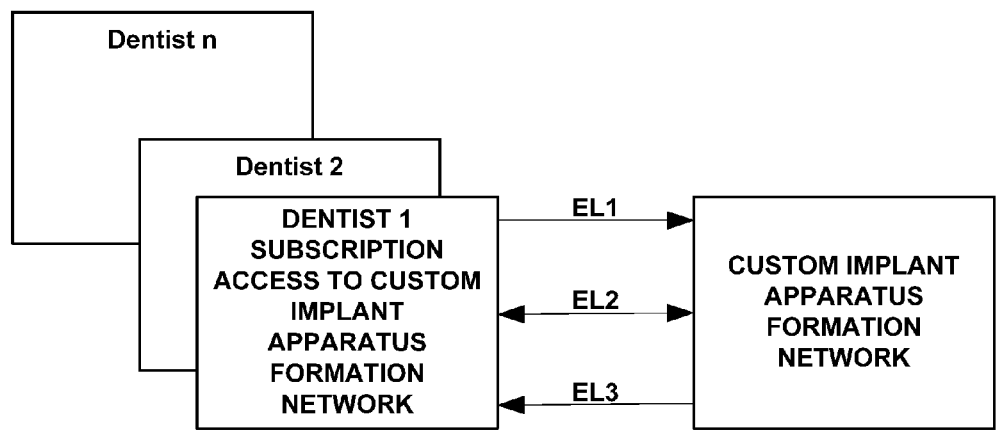
FIG. 23 is a flow diagram of a subscription access e-learning process for an improved system and method for the design, creation and installation of implant-supported dental prostheses according to one embodiment of the present invention.

FIG. 23 illustrates three aspects of the e-learning elements for a dentist subscriber. EL1 represents the conveying of a learning into the system. EL2 represents interactive collaboration between a dentist subscriber and others, e.g. another dentist subscriber or at least one member of a team of experts. EL3 represents the conveying of a learning from the system to a dentist subscriber.

Figure 24:
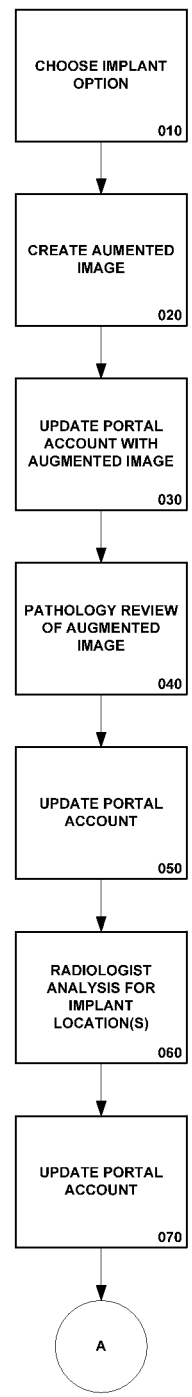
FIG. 24 is a flow diagram showing detail of a portion of a product and services process for an improved system and method for the design, creation and installation of implant-supported dental prostheses according to one embodiment of the present invention.

FIG. 24 illustrates an example of steps in a process in an embodiment of an improved system and method for the design, creation and installation of implant-supported dental prostheses. In step 010 a dentist and a patient agree on an implant procedure, the patient is referred to a system imaging center and an account is created for the patient in a portal data base. In step 020, an image is made of the patient's mouth, utilizing enhanced image technology, e.g. cone beam based technology. In step 030, the enhanced image is updated into the patient's account. In step 040, a pathology review is made for the enhanced image. In step 050, the annotated review is updated into the patient's account. In step 060 a radiologist analysis is made on a recommended implant(s) placement for the patient. In step 070, the patient's account is updated with the recommendations.

Figure 25:
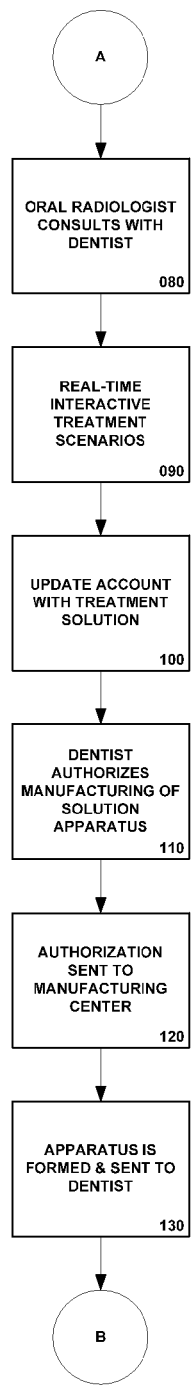
FIG. 25 a flow diagram showing detail of a subsequent portion of a product and services process for an improved system and method for the design, creation and installation of implant-supported dental prostheses according to one embodiment of the present invention.

FIG. 25 illustrates an example of subsequent steps for FIG. 5. In step 080, an oral radiologist consults with the dentist. In step 090, the dentist and the radiologist may interactively explore alternatives by manipulating the implant data in real time. In step 100 the final approach decided by the dentist is updated to the patient's account. In step 110 the dentist authorizes the manufacture of a drill guide based on the final approach. In step 120 the data needed to form the drill guide is sent to a manufacturing center. In step 130, the drill guide kit is manufactured and shipped to the dentist for performing the procedure.

Figure 26:
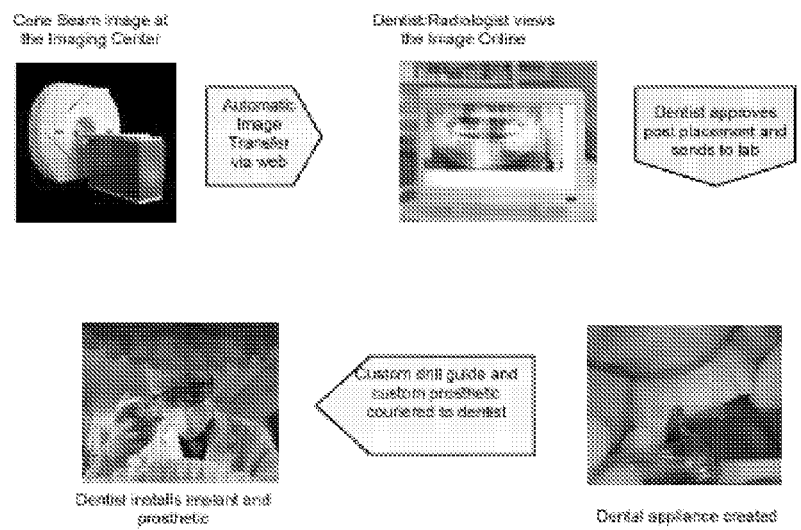
FIG. 26 is a flow diagram illustrating a summary of an improved system and method for the design, creation and installation of implant-supported dental prostheses according to one embodiment of the present invention.

FIG. 26 illustrates one embodiment of the product and services process.

Figure 27:
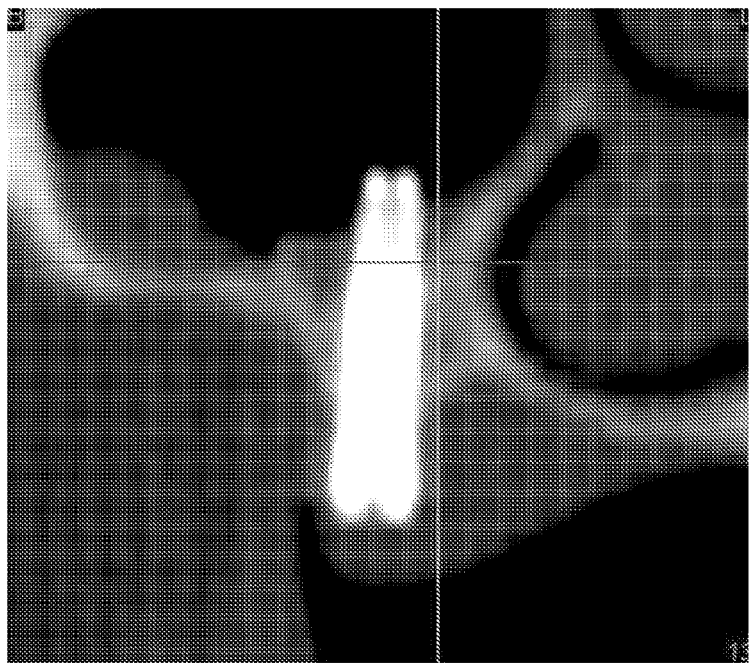
FIG. 27 illustrates one of the problems that may occur without the use of data provided by the present invention.

FIG. 27 illustrates an implant improperly placed in a patient.

Figure 28:
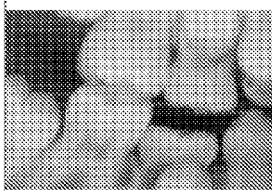
FIG. 28 illustrates a home web page for an improved system and method for the design, creation and installation of implant-supported dental prostheses according to one embodiment of the present invention.

FIG. 28 illustrates an entrance page that enables communications between a dentist and Advanced Dental Technologies team of experts. This team will support, via the internet, all aspects of diagnosis, treatment planning, and manufacturing of custom "one off" body parts for dental implant therapy, orthodontic therapy, endodontic therapy, oral surgery therapy, plus any associated orthopedic therapy for respective dentists and medical doctors.

Figure 29:
FIG. 29 illustrates an explanation web page for an improved system and method for the design, creation and installation of implant-supported dental prostheses according to one embodiment of the present invention.
Figure 30:
FIG. 30 illustrates a log in web page for an improved system and method for the design, creation and installation of implant-supported dental prostheses according to one embodiment of the present invention.

FIG. 29 illustrates a simplified illustration of an embodiment of a process for This page creates a simplified visual of the Advanced Dental Technologies process for an improved system and method for the design, creation and installation of implant-supported dental prostheses FIG. 30 illustrates an initial level of customer or potential customer identification into an embodiment of a system for an improved system and method for the design, creation and installation of implant-supported dental prostheses.

Figure 31:
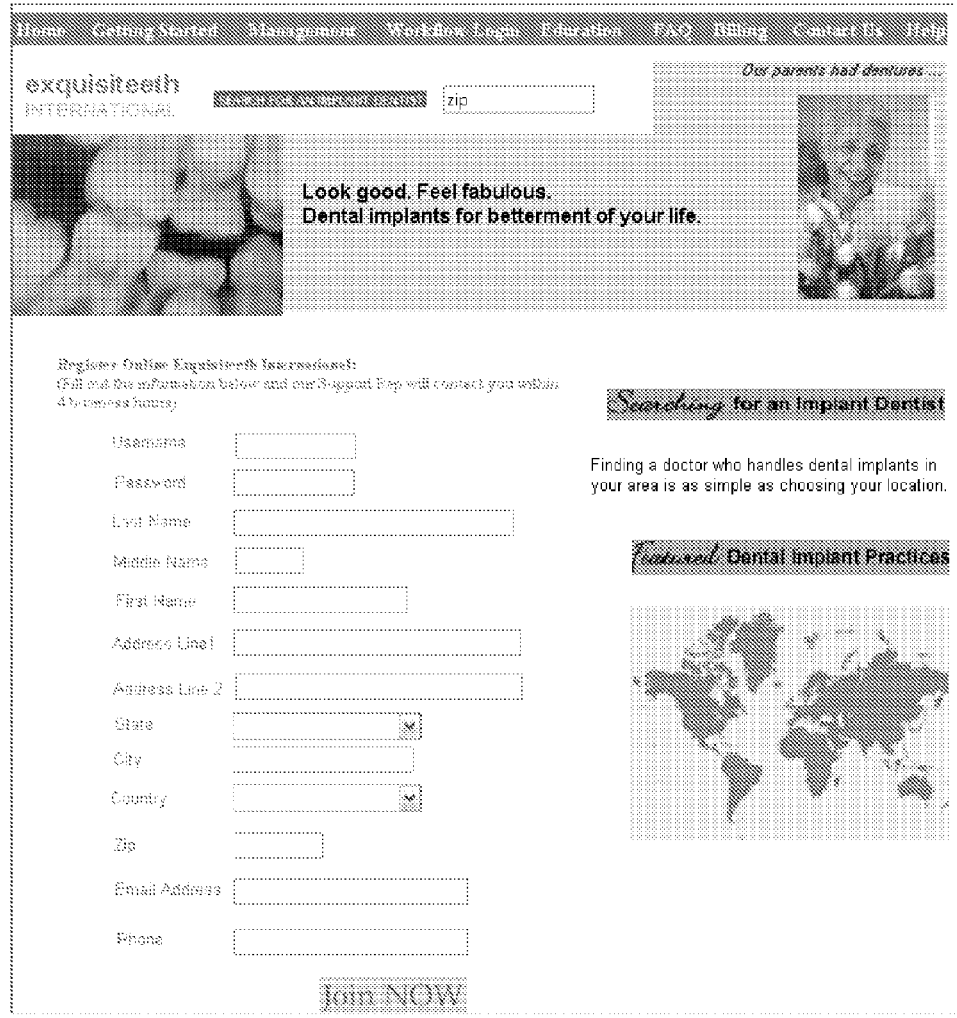
FIG. 31 illustrates a contact us web page for an improved system and method for the design, creation and installation of implant-supported dental prostheses according to one embodiment of the present invention.

FIG. 31 illustrates an initiation for multi-leveled support and education with an embodiment of a process for an improved system and method for the design, creation and installation of implant-supported dental prostheses.

Figure 32:
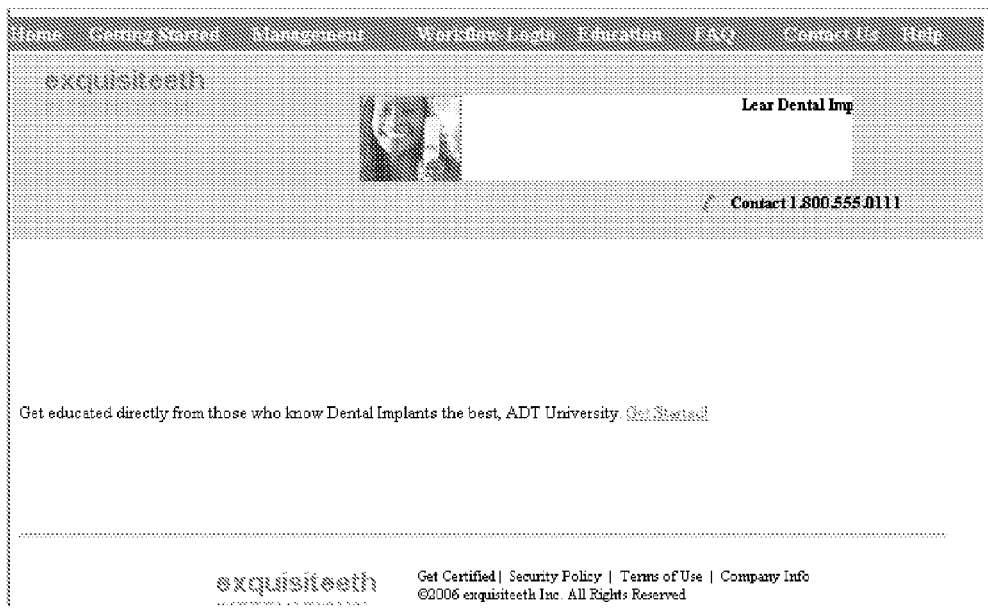
FIG. 32 illustrates an e-learning getting started web page for an improved system and method for the design, creation and installation of implant-supported dental prostheses according to one embodiment of the present invention.

FIG. 32 illustrates an introduction to an embodiment of an educational process for practitioners of dental specialties utilizing an embodiment of a portal for an improved system and method for the design, creation and installation of implant-supported dental prostheses.

Figure 33:
FIG. 33 illustrates an frequently asked questions (FAQ) web page for an improved system and method for the design, creation and installation of implant-supported dental prostheses according to one embodiment of the present invention.

FIG. 33 illustrates a frequently asked questions page supporting patients who will have dental imaging for applicable specialties in an embodiment of a process for an improved system and method for the design, creation and installation of implant-supported dental prostheses.

Figure 34:
FIG. 34 illustrates a technical support web page for an improved system and method for the design, creation and installation of implant-supported dental prostheses according to one embodiment of the present invention.

FIG. 34 illustrates an embodiment of a technical support page that provides access to a structured level of radiological and dental implant therapy support for a dentist and his or her staff. This support may start out with no cost assistance with simple technical questions all the way to consultation with high level dentists in the radiology and implant specialties.

Figure 35:
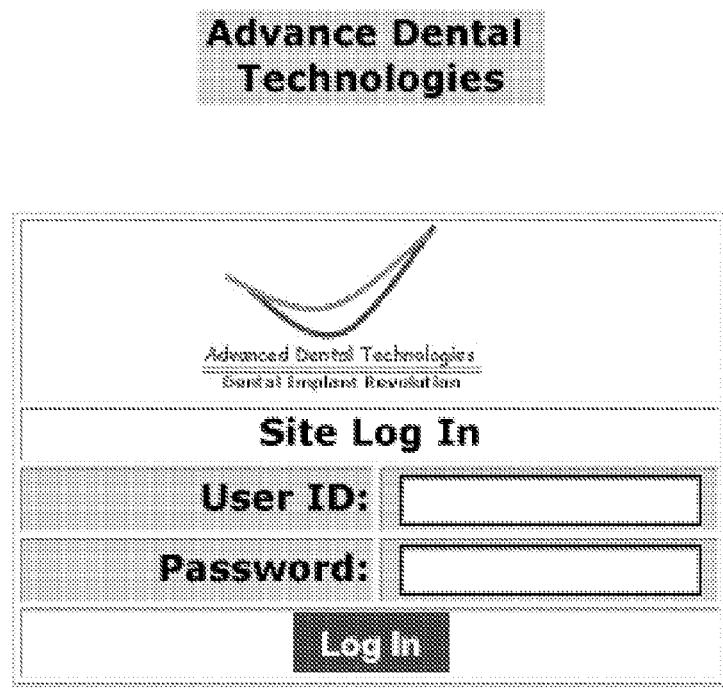
FIG. 35 illustrates a password protected log in web page for an improved system and method for the design, creation and installation of implant-supported dental prostheses according to one embodiment of the present invention.

FIG. 35 illustrates a page which allows a dentist protected and exclusive access to all information and communication capabilities within an embodiment of a network for an improved system and method for the design, creation and installation of implant-supported dental prostheses. This secure login acts as a tracking device that initiates the security and individualization necessary to manage patients' records and files accurately.

Figure 36:
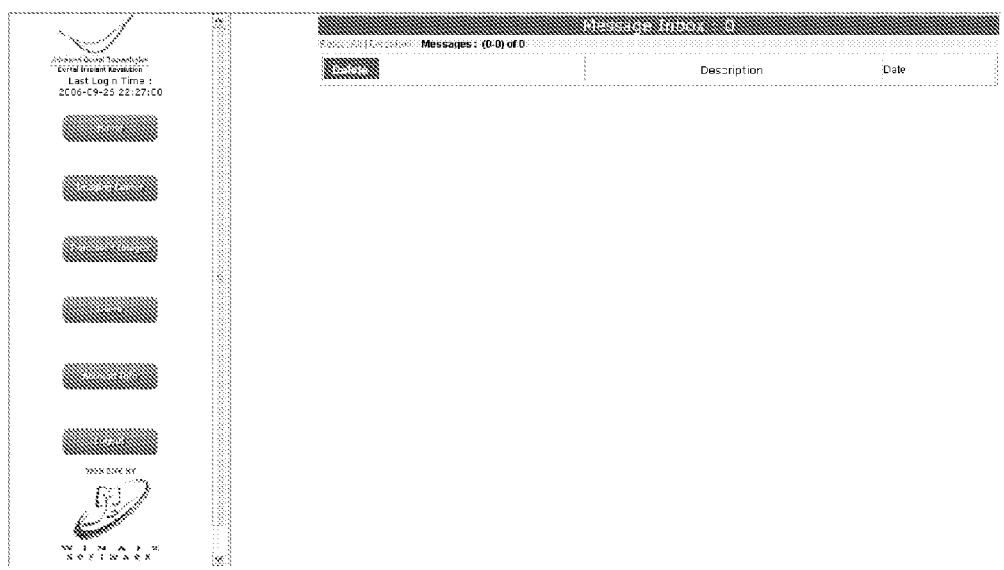
FIG. 36 illustrates an image data input web page for an improved system and method for the design, creation and installation of implant-supported dental prostheses according to one embodiment of the present invention.

FIG. 36 illustrates an embodiment of a web page which allows customers of the system, as well as a team of experts, access to input all applicable information in any way necessary to complete the total process for all applications of the image data software data management.

Figure 37:
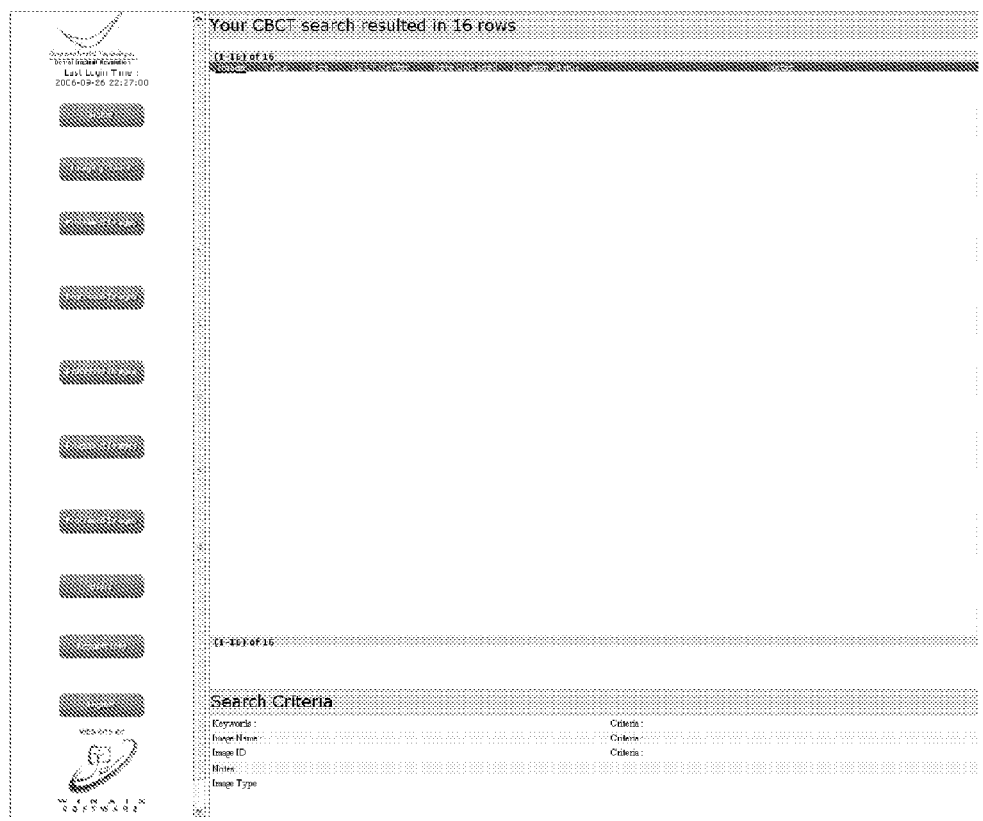
FIG. 37 illustrates an image data search web page for an improved system and method for the design, creation and installation of implant-supported dental prostheses according to one embodiment of the present invention.

FIG. 37 illustrates a web page which allows customers of the system, as well as a team of experts access to search all applicable information in any way necessary to complete the total process for all applications of the image data management.

Figure 38:
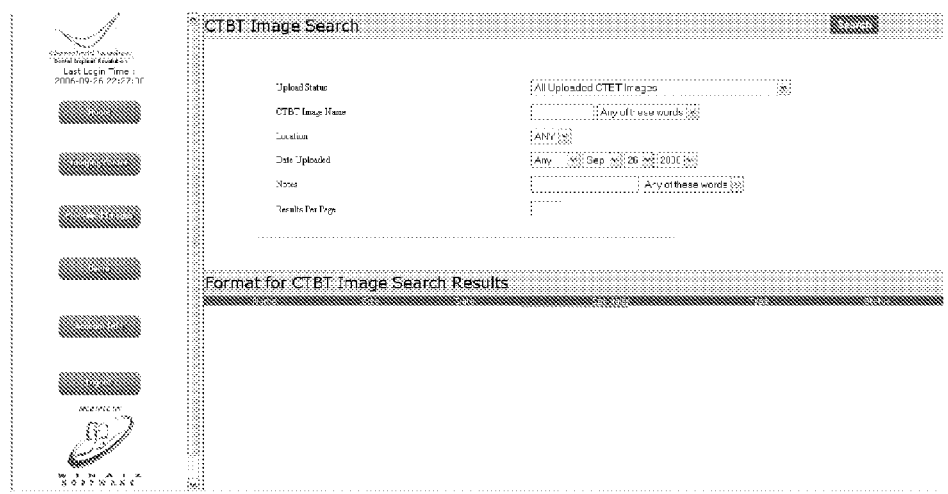
FIG. 38 illustrates an alternate view of an image data search web page for an improved system and method for the design, creation and installation of implant-supported dental prostheses according to one embodiment of the present invention.

FIG. 38 illustrates a web page similar to FIG. 37 presented in a slightly different format.

Figure 39:
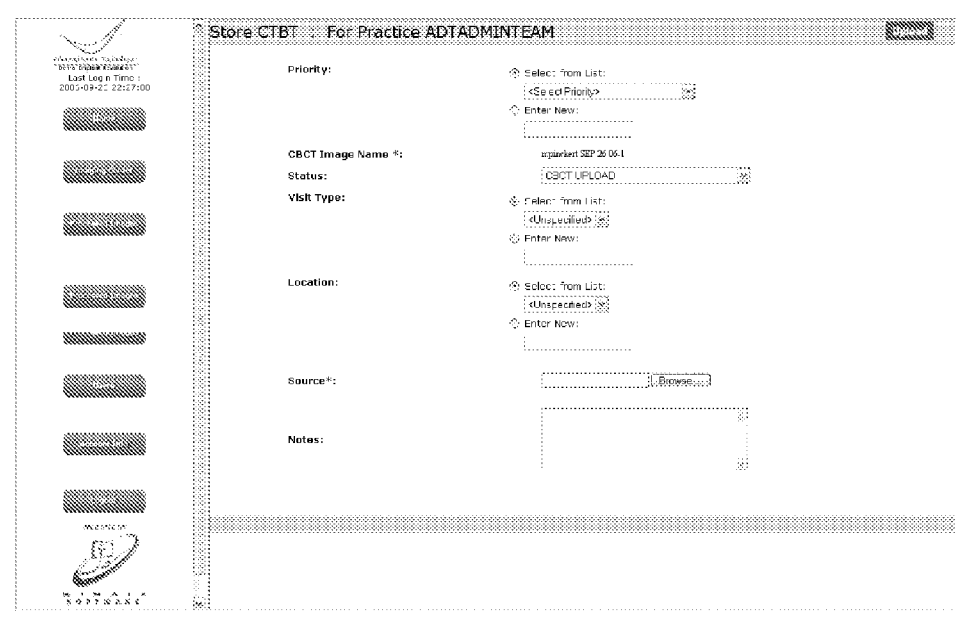

FIG. 39 illustrates a web page used to introduce image data into an embodiment of a data management system. This data management system may be utilized by an administrator in a system owned imaging center, or by any imaging device owned by a dentist office, doctor's office, or commercial imaging facility.

Figure 40:
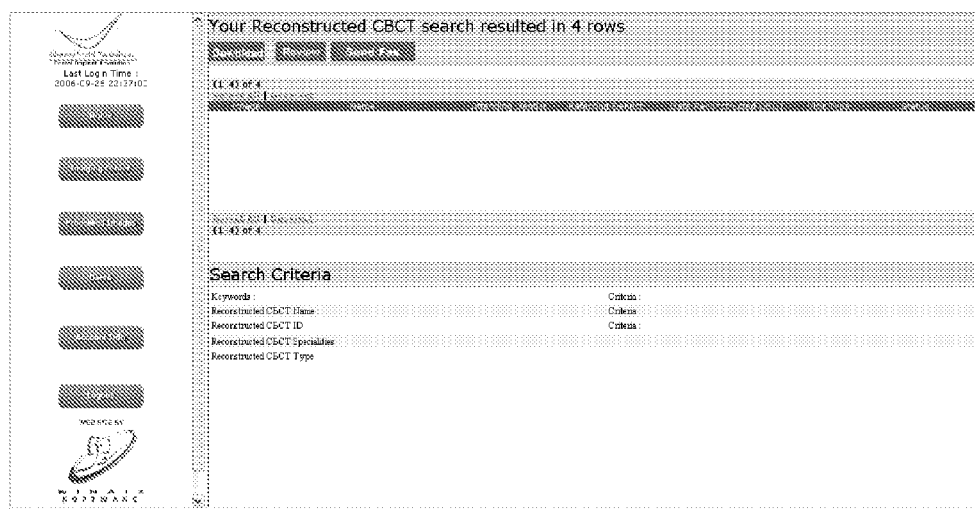
FIG. 40 illustrates a searching mechanism for reconstructed image data files web page for an improved system and method for the design, creation and installation of implant-supported dental prostheses according to one embodiment of the present invention.

FIG. 40 illustrates a searching mechanism for manipulated data resulting from a system team of experts carrying out the functions associated with the "start to finish" management of image data. This system may be used by customers of an embodiment of a system or by a system's team of experts.

Figure 41:
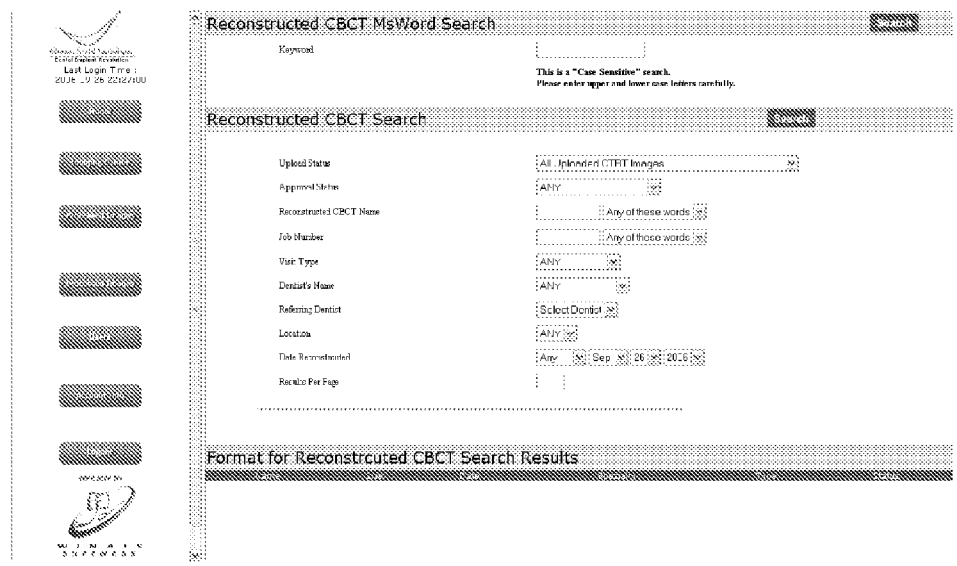
FIG. 41 illustrates a word search mechanism of reconstructed image data files web page for an improved system and method for the design, creation and installation of implant-supported dental prostheses according to one embodiment of the present invention.

FIG. 41 illustrates a searching mechanism for manipulated data resulting from a team of experts carrying out the functions associated with the "start to finish" management of image data utilizing a word search. This may be used by customers of the system or its team of experts.

Figure 42:
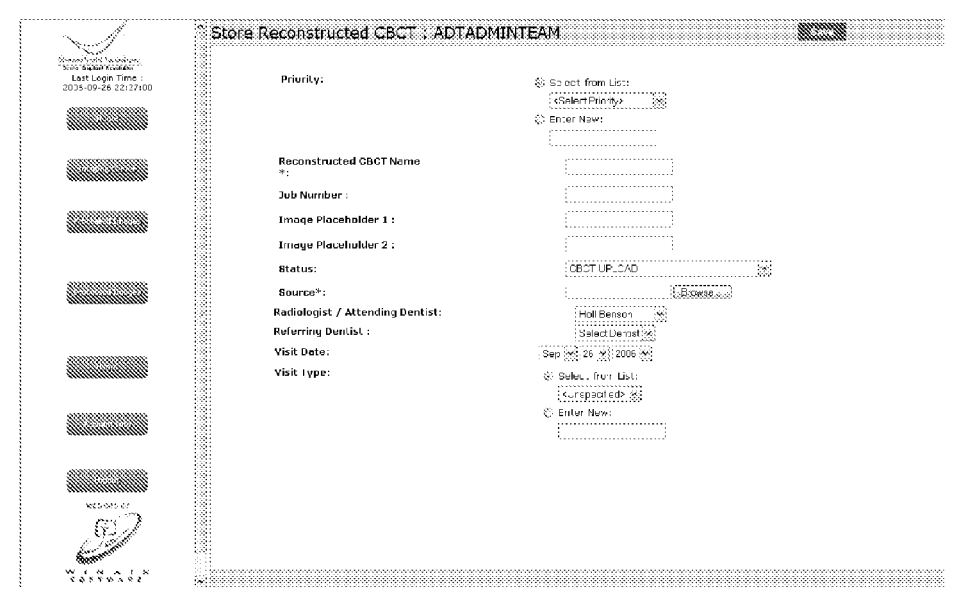

FIG. 42 illustrates a storage mechanism for data images of customers of the system that meets all lawful requirements associated with management of such data.

Figure 43:
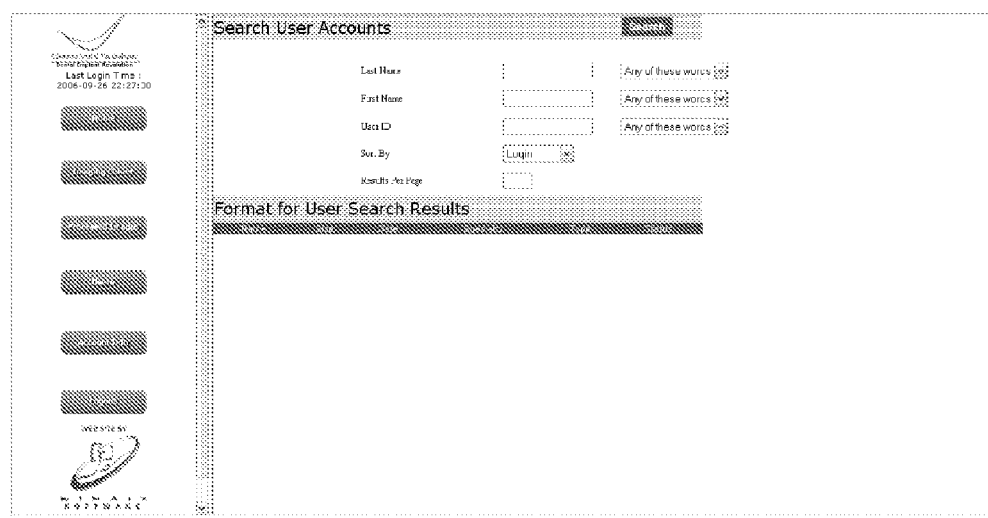
FIG. 43 illustrates a search user accounts web page for an improved system and method for the design, creation and installation of implant-supported dental prostheses according to one embodiment of the present invention.

FIG. 43 illustrates a searching mechanism for access to data stored in the files of customers of the system and data bases.

Figure 44:
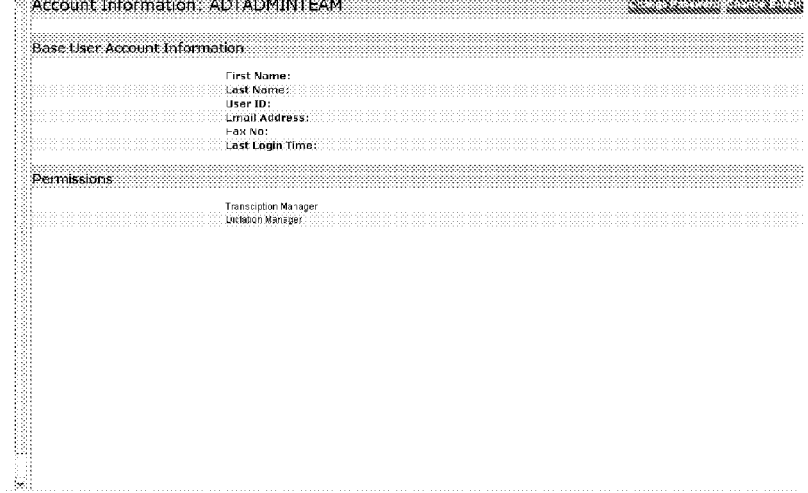
FIG. 44 illustrates an account information for an admin team web page for an improved system and method for the design, creation and installation of implant-supported dental prostheses according to one embodiment of the present invention.

FIG. 44 illustrates an account creation, tracking, billing and file sharing mechanism that is interactively used by the entire team.

Figure 45:
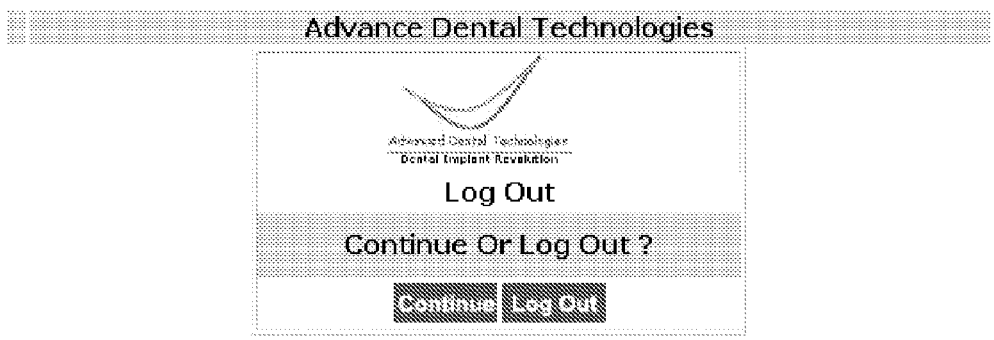
FIG. 45 illustrates a log out web page for an improved system and method for the design, creation and installation of implant-supported dental prostheses according to one embodiment of the present invention.

FIG. 45 illustrates a secure exit from an embodiment of a website used by customers and the support team experts.

Figure 46:
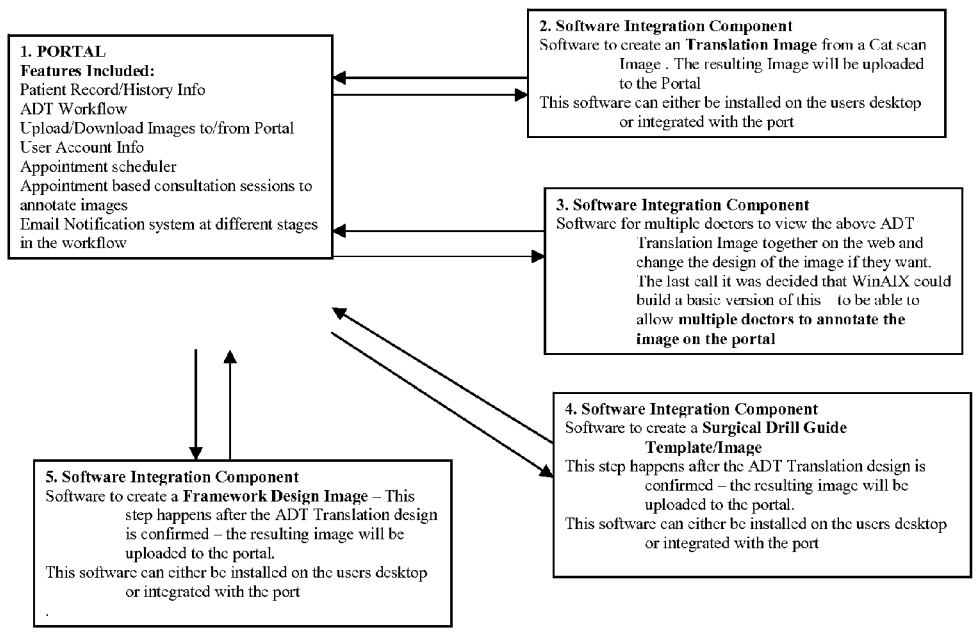
FIG. 46 illustrates a software arrangement for an improved system and method for the design, creation and installation of implant-supported dental prostheses according to one embodiment of the present invention.

FIG. 46 illustrates one embodiment of software components for an improved system and method for the design, creation and installation of implant-supported dental prostheses.

Figure 47:
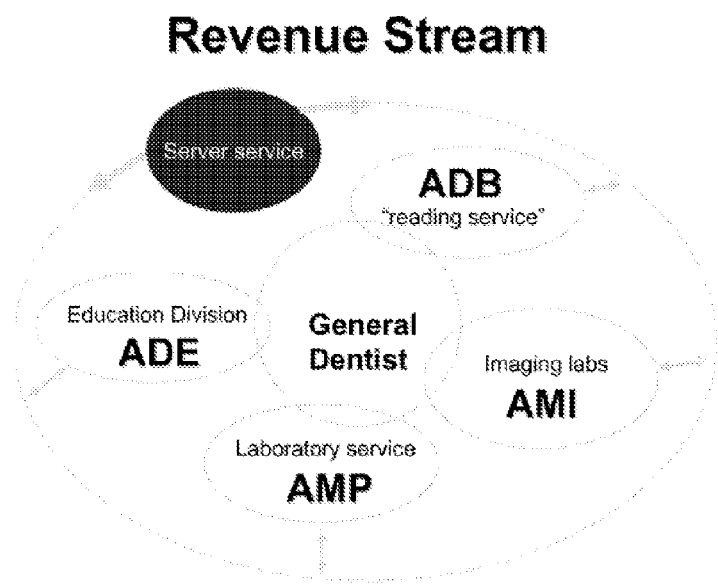
FIG. 47 illustrates a financial arrangement for an improved system and method for the design, creation and installation of implant-supported dental prostheses according to one embodiment of the present invention.

FIG. 47 illustrates the financial relationships between the portal, i.e. server service, and a dentist, an imaging lab, a reading service, a laboratory service and an educational service for an embodiment of an improved system and method for the design, creation and installation of implant-supported dental prostheses.

Figure 48A:
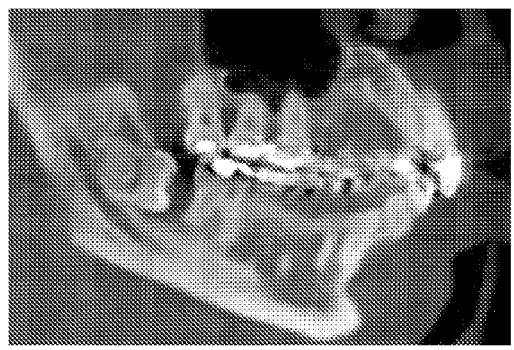
FIG. 48A illustrates a view of a patient's teeth and jaw using conventional X-ray technology.
Figure 48B:
FIG. 48B illustrates a view of a patient's mouth using Cone-Beam technology.

FIG. 48 illustrates the limitations of using dental X-rays.

Figure 49:
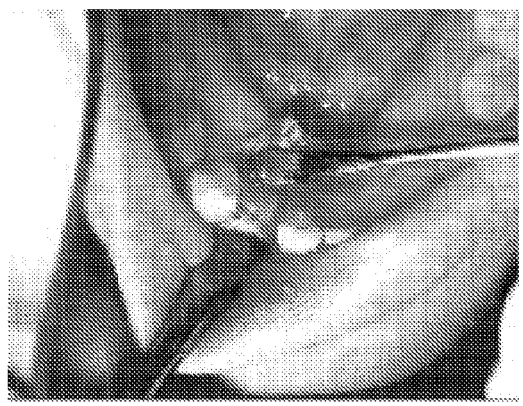
FIG. 49 illustrates a "Braille technique" for implant-hole placement.

FIG. 49 illustrates an implant procedure without using a drill guide.

Figure 50:
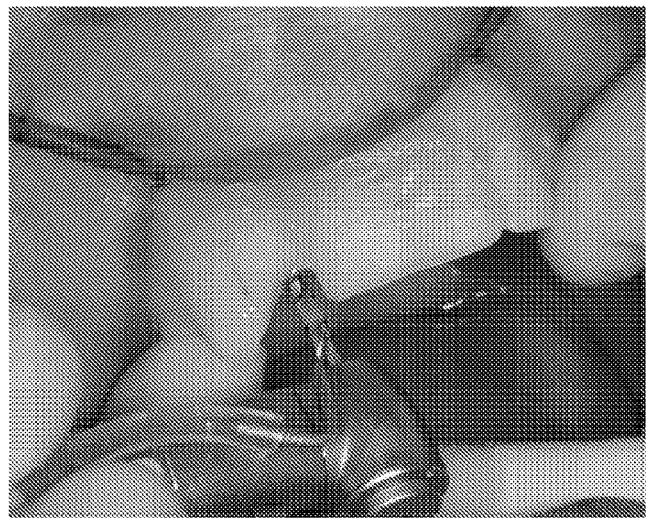
FIG. 50 illustrates using a drill guide to form an implant-hole.

FIG. 50 illustrates an implant procedure using a drill guide.

Figure 51:
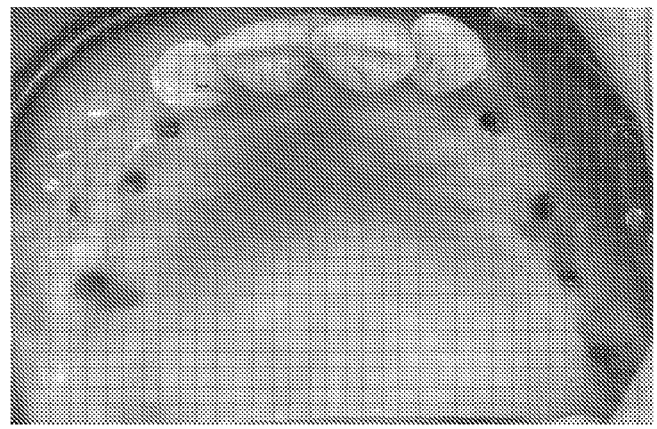
FIG. 51 illustrates an image guided technique for implant-hole placement.

FIG. 51 illustrates the results of using a drill guide during an implant procedure.

In one embodiment of the present invention the following steps are applied:

Step 1. Patient visits Dentist—impressions and a record of at-rest jaw spacings is created. A drill-guide impression tray (for a full jaw) is used to take an impression of the jaw that will receive the prosthesis. This drill-guide tray is similar to trays employed to hold impression compound while it hardens, during conventional full-jaw impressions, and which may later serve to create a positive cast (mold) of the jaw. This tray, however, is first used to create an impression, later accurately refitted to the patient's jaw, and there serves as a simple guide for drilling cavities for the patient's implants. It is anticipated to be precision-formed, but a production item. Its surface, on the side away from the trough that holds impression compound, is embossed with flat raised areas in some pattern that will be accurately defined in a high-resolution scan. They will later be used as position markers for drilling guide-holes through the tray. Impressions are sent to the Lab.

Step 2. The patient now visits a special Imaging Clinic, with which his Dentist may be affiliated as a means of sharing the costs of owning and operating the equipment. A Cone Beam scan is made of the patient's jaw region. A scan is also made of the drill guide tray. (If preferred, the drill guide tray jaw impression could be made at the Imaging Clinic rather than by the Dentist). The 3D scan data are stored on the Clinic's storage drives, whose contents are available to authorized users through the shared secure Web Portal.

Step 3. The patient's Cone Beam scan data is reviewed by a pathologist, using software of the type delivered with Cone Beam scanners intended for head-scans. If any pathology is observed in the Cone Beam data, the patient's Dentist is informed, and a specialist may be suggested for needed preliminary work. If no pathology is observed (or after treatment if needed), the Dentist, or alternatively an Implant Technologist determines appropriate implant locations in the jaw area to support a prosthesis.

Step 4. Data required to later complete a drill guide is prepared, using data from the Cone Beam scan of the patient. This is a two-part process. The first part, optimizing implant placements, is explained here, the second is explained in connection with Step 5. Using software designed explicitly for the purpose, the user first views the patient's Cone Beam scan data, viewing the top surfaces of teeth in the jaw that will receive implants. The opposite jaw is made not visible. The user orders a new virtual implant to be set up by a command to the software. Location is initially in an area of the screen outside the jaw area, but by use of the mouse or a similar computer-pointer device, the virtual implant can be moved wherever needed in the visual display of the jaw. Each time the virtual implant is moved by the user, the software re-combines the 3-dimensional data of the jaw with that of the implant. (This is a straightforward step in 3D software.) The implant appears initially at an orientation perpendicular to the chewing surface. When it has been (virtually) moved to its chosen site in the jaw—that is, the image representing it has been moved to a position on the computer display corresponding to a location on the teeth seen in the display—another command will cause the implant to be moved (up or down) to a "final" position below the virtual gum line. The entire virtual jaw image can be rotated (in both latitudinal and longitudinal directions), and returned quickly to a standard view, in which the implant orientation can be adjusted. Orientations other than the normal one can be memorized, so they can be returned to quickly. Because in the Cone Beam data, density of different tissues can be distinguished, the implant can be viewed from various angles to insure that it will be seated in bone adequate to support it. It is now possible to change the orientation (of virtual implant in virtual jaw) from "vertical" to other angles, so as to find an orientation at which the actual implant would be entirely in bone, well-centered in the bone mass. If the length of the (virtual) implant used for position determination is incorrect, another command will replace it with a longer (or shorter) implant from a list of available implant lengths, leaving the prosthesis end of the implant at a fixed position during the change. It will be possible to view the implants in the bone with the flesh not being visible, as a further check on placement. When one implant's position has been determined to the satisfaction of the user, he or she can select the next, and repeat the steps in any order. The program will contain dimensional characteristics of implants from various sources and of various styles. The Dentist's Mounting Record, in addition to showing the relationship of the patient's jaws in the closed position, should also indicate spacings in the widest open position in which the patient can be comfortable, to enable checking maximum usable implant lengths, especially if implant locations in the rear part of the jaw are needed.

Step 5. Lab makes jaw models from impressions. Lab then creates a drill guide from the jaw impression captured earlier. Models are then assembled with correct jaw spacings, and 3D-scanned to define the virtual space into which the prosthesis must fit. The Cone Beam scan of the drill guide tray with jaw impression is rotated, scaled (necessary, for example, if its scan was made by an Cone Beam scanner with different 3D cell size from that used to capture the patient's in vivo data) and shifted to merge it with the data for jaw and virtual implants. All that is needed by way of implant location data are the position, angle and depth of entry through the surface of the drill guide tray, whose raised areas serve as alignment points when it is placed on a mating jig in a numerically controlled drill having two-dimensional angular orientation. The thickness of the tray can be increased, before drilling it, by addition of thickening metal plates or a precisely formed metal shell to the tray, or by local add-on layers that will create a longer guide tube for the bone drilling, and possibly a larger-diameter opening in which to inserting the tip of the bone drill. These additions, of course, may not intrude on the areas of the tray by which it is positioned to the jig, on the drilling machine which prepares the guide holes. Since the drill-guide tray is rigid and contains aligning areas on its surface, programming the drilled holes can be done automatically using relatively simple trigonometric calculation. When the drill guide is completed, it should be thoroughly de-burred in a traditional way. It is desirable to add small air-relief holes through the tray to ease seating of the completed drill guide to the jaw. (Alternatively if material usable as an impression compound had a degree of porosity that might be a suitable alternative to relief holes.) The drill guide provides location and orientation for each implant. A depth specification for each implant is also needed. This will be specified numerically (for example, in millimeters) when the drill guide is prepared, and preferably marked permanently on the guide. If the Dentist's preparation tool has an adjustable depth-limiting collar, that can be set during preparation. Alternatively simple depth-indicating metal- or plastic-pin gauges can be supplied with each gauge marked and of correct length corresponding to the depth of the preparation for one planned implant. As another alternative, the Dentist can be supplied with a simple metal-rod depth gauge having a sliding sleeve. When the pin is pushed to the bottom of the preparation, the sliding sleeve will be pushed back so as to remain flush with a reference face on the drill guide. The visible length between the sleeve and the end of the pin is then compared with the planned depth.

Step 6. The Dentist prepares holes for all implants, using the drill guide to prepare cavities, and removing it before installing them if necessary for clearance of the implant head and wrench. Healing abutments are finally installed, using screws into the implants. The patient's gums are sutured where necessary to healing. There may then elapse a healing period so that the implants can integrate firmly into the bone of the jaw.

Step 7. The Dentist makes an impression of the implanted jaw including the healing abutments. This is necessary because as-installed-and-healed positions and orientations of implants may differ slightly from preplanned values. This impression is forwarded to the Lab.

Step 8. The Lab Cone Beam-scans the impression of the implanted jaw, after healing if it was required. 3D data from this scan and the existing (in vivo) opposing-jaw data are now used to create a virtual model of a frame for the prosthesis. Lower-cost procedures may be feasible using relatively simple optical or other scanning methods, since the concern is exact location of the attachment faces of the implants and the tissue around them. All of these are in direct view on an impression, if healing abutments extend above the gum. The scans of the (impression of the) implanted jaw and that of the opposing jaw of the patient are merged using graphics software. This requires modification of the implanted-jaw data to show the impression as if solid tooth material, the tray and the space below its trough as empty. Another modification is made in the implanted-jaw data, namely the removal of the healing abutments. Since these are of known size and shape, this is a matter of locating the part of the data representing the outer face of an abutment, estimating a line normal to it and shifting the face inward by the thickness of the abutment. A user can locate the abutment outer face in much the same way current photo-retouching software finds "red-eye", i.e. by having the user select the area. The next step is to "close" the virtual jaws. The virtual upper and lower jaws are moved close together (manipulating only one virtual jaw), with tooth-to-tooth overlap being shown in a high-visibility color on the conventional 2D display of the two virtual objects, until a correct at-rest position is located by a combination of visual appearance of the teeth compared to photos, and a uniform near-zero virtual overlap seen. This alignment may lend itself to automation, though five dimensions need to be adjusted (two positions, two rotations and spacing. In a manual adjustment, the operator should see many lower and upper teeth nearing contact simultaneously (and "lighting up" in the virtual view where near-contact is reached) may provide valuable insights better than initially possible in an automated optimization. Since there is slight uncertainty in the positions of tooth surfaces due to the finite cell size of the Cone Beam data, teeth nearly in contact will display an apparent slight overlap, the shape of that an indication of how the teeth abut one another. When a "jaws closed, psychological rest" jaw relationship has been achieved, the combined model reveals between the implanted jaw and its opposing jaw, the space into which the prosthesis must fit. It should be noted that healing abutments are rounded rather than sharp-edged, on the ends that face the prosthesis. This works against achieving accurate measurements of the orientation angles of implants. Since those angles were optimized during preparation of the drill guide, if the guide was used to drill sockets for the implants they should be implanted at or near the predetermined angles, which can easily be used introduced into the data for the implanted jaw. Now that a virtual model of the space available and the attachments points for the prosthesis is defined, the frame can be designed. Some of the methods evolved for Rapid Prototyping of U.S. Defense Systems are well suited to this task. Earlier frames have been very heavy and stiff, their object being to render the entire assembly, implants and frame both immovable and unbendable. The jaw, with its teeth set into softer tissue and surrounded by muscle is naturally elastic, though clearly to a limited degree. At some time in the near future, if the construction capability exists, it seems likely that prostheses—especially large ones, may be expected to benefit from certain elasticity, for example, through enhanced useful lifetimes. While the detailed nature of that elasticity is not yet understood, we propose here a design paradigm that can adapt to a wide variety of structural needs. There are two basically different techniques for forming complex industrial parts: additive and subtractive. The technique most often used, since the start of the industrial revolution (and millennia before, in stone sculptural work), involves subtractive cutting. A solid billet of metal, larger in every dimension than the final item, is cut away until what remains is the specified part. In additive forming techniques, the needed part is assembled from small pieces, without appreciable waste. Traditionally, dental prosthetics have largely been additively created, though metal casting has also played a major role. One of the techniques developed as a means of rapidly prototyping a complex part involves building a model of it as a stack of thin sheets (usually of plastics), each cut rapidly and automatically using lasers and stacked automatically, each thinly coated with a heat-activated adhesive to hold the stack together. The stacked structure is then used as a mold, to cast the actual part—in this case, a prosthesis frame—in a metal or alloy. The mold is destroyed in the process. As in any casting process, additional elements are added to form sprue holes, to ensure that all parts of the final casting are metal-filled. In the technique described, the sprue areas may also serve to connect different parts in one layer of the stack that would; otherwise; be unconnected. This technique can be used to form shapes more complex than traditional manual design techniques can conveniently specify. Unlike a heavy solid bar frame, strength here is produced by combination of a relatively light outer shell, cylinders provided for attachment to the implants, and integral metal septa carrying biting and chewing forces from the shell to the implants. The frame also serves as a platform for artificial teeth and a support for the plastic material that adapts the prosthesis to the adjacent gum and to the artificial teeth it holds in position. Though current dental prosthesis practice creates a rigid assembly of frame, surrounding thermoplastic artificial "gum" and artificial teeth, future designs may incorporate controlled elasticity in their design. Frame structures similar to that shown in FIG. 4 can provide this opportunity, through purposely flexible frame design and incorporation of elastic material supporting the "teeth". Design of shapes to be constructed by lamination of thin plastic sheets must be converted into outlines of a series of sheets, most of them different from the one preceding and following. The frame shape is described using a computer program that takes into account this laminated construction. Subsequently, the program designs each layer. This may be done dynamically, in a cutting and stacking machine that forms and assembles layer in turn. Conventional foundry methods can be used to cast the frame.

Step 9. The Lab or a specialist contractor creates the frame using a Rapid Prototyping technique, as described above.

Step 10. Lab personnel use traditional dental-prosthesis methods to properly place artificial teeth, artistically fill in resin around the frame, representing gum tissue, and finally, drill out implant screw access holes through the biting or chewing surfaces, to the frame. With currently available technology, this step would be performed manually, using physical impression-based models of the patient's jaws.

Step 11. The Dentist removes healing abutments or any other temporary structures near the implants then installs the prosthesis in the patient's mouth. If necessary, slight "milling in" adjustments will be made if needed, but with precision design and construction of the prosthesis, this should be minor. Resin is used to fill the attaching screw access-holes.

The steps described above, it should be understood, represent one embodiment of the present invention, one incorporating currently available technology and construction methods. With future changes in materials, measuring techniques, the design of prostheses, or other aspects, it can be expected that this sequence may change to some degree. Since this patent application relates to the use of modern measuring instrumentation, automation and use of high-bandwidth communications to move patient data anywhere needed, it also anticipates and incorporates these changes in materials, design and construction of prostheses, as well as the economics, capabilities, and even the underlying phenomenology of electronic scanning and imaging equipment. Reduction in cost of scanning/imaging equipment, or the use of low-cost high-resolution imaging equipment based on use of non-harmful radio waves (for example), might move most patient measurement into the dentist's office or possibly do away with need to use physical models as intermediate measurement devices, as described in the above embodiment. It is, for example, possible that physical models might economically be created from Cone Beam scan data using the same stacked-laminations technique described above for frame construction.

From the foregoing, it will be appreciated that, although specific embodiments of the invention have been described herein for purposes of illustration, various modifications may be made without deviating from the spirit and scope of the invention. For example, many of the features and components described above in the context of a particular improved system and method for the design, creation and installation of implant-supported dental prostheses configuration can be incorporated into other configurations in accordance with other embodiments of the invention.

What is claimed is:

1. A computer-assisted method of creating a dental implant prosthesis, comprising the steps of:
scanning a target jaw area where a patient needs a tooth implant, using a three-dimensional imaging device to produce three-dimensional scan data, and creating a three-dimensional digital representation of the target jaw area including representations of upper and lower jaws by processing said three-dimensional scan data using a computer operably connected to receive said scan data from said three-dimensional imaging device;
displaying said three-dimensional digital representation for an operator, performing computer-assisted analysis of the digital representation to generate information relevant to selecting implant placement, displaying said information relevant to selecting implant placement, and receiving an electronic input from the operator selecting an implant placement location in response to said display of said digital representation and implant placement information;
using a computer, processing said digital representation of said jaws to create a digital simulation of a closed position of said jaws and electronically calculate boundaries of a space available for an implant prosthesis at the implant placement location when the jaws are closed; electronically generating a three-dimensional digital model of said implant prosthesis based on said calculated boundaries and electronically transmitting said digital model to an automated manufacturing system whereby said automated manufacturing system is enabled to generate the implant prosthesis configured to fit the selected implant placement location according to said digital model.

2. The method of claim 1 including the further step of electronically generating a digital design for automated manufacturing of a custom drill guide corresponding to said implant placement and transmitting said digital drill guide design to an automated manufacturing system whereby said automated manufacturing system produces the custom drill guide.

3. The method of claim 1 wherein the step of scanning a target jaw area uses cone beam imaging technology.

4. The method of claim 1 including the further steps of:
electronically transmitting information defining the proposed implant placement to a dentist; and
receiving approval from the dentist of the proposed implant placement and recording the approval electronically.

5. The method of claim 1 wherein the proposed implant placement includes a proposed length of an implant post.

6. A computer-assisted method of creating a dental implant prosthesis, comprising the steps of:
scanning a target jaw area where a patient needs a tooth implant, using a three-dimensional imaging device to produce three-dimensional scan data, and creating a three-dimensional digital representation of the target jaw area including representations of upper and lower jaws by processing said three-dimensional scan data using a computer operably connected to receive said scan data from said three-dimensional imaging device;
using a computer, processing said digital representation of said jaws a to create a digital simulation of a closed position of said jaws and electronically calculate boundaries of a space available for placement of an implant prosthesis when the jaws are closed, and electronically generate a three-dimensional digital model based on said calculated boundaries; and
electronically transmitting said digital model to an automated manufacturing system whereby said automated manufacturing system is enabled to generate said implant prosthesis configured according to said digital model.

7. The method of claim 6 including the further step of electronically generating a digital design for automated manufacturing of a custom drill guide corresponding to said implant placement, using a computer, and electronically transmitting said digital drill guide design to an automated manufacturing system whereby said automated manufacturing system is enabled to produce the custom drill guide.

8. The method of claim 6 wherein the step of scanning a target jaw area uses cone beam imaging technology.

9. The method of claim 6 including the further steps of:
electronically transmitting information defining the proposed implant placement to a dentist; and
receiving approval from the dentist of the proposed implant placement and recording the approval electronically.

10. The method of claim 6 wherein the proposed implant placement includes a proposed length of an implant post.

11. An automated computer system for creating an implant for use by a dentist, comprising:
at least one digital processor;
at least one electronic memory element operably connected to said digital processor;
a digital image data interface that electronically receives and stores in said at least one electronic memory element a three-dimensional digital representation of a target jaw area where a patient needs a tooth implant, said three-dimensional digital representation including electronic data representations of upper and lower jaws, calculated based on a digital data output of a three-dimensional imaging scan of the target jaw area;
an implant determination program element operating in said at least one digital processor that receives and stores digital information defining at least one proposed implant placement relative to the target jaw area, said implant placement derived from analysis, using the processor, of said three-dimensional digital representation;
a digital simulation program element operating in said at least one digital processor and comprising instructions that cause said at least one digital processor to electronically receive jaw structure data from the digital image data interface and automatically create a digital simulation of a closed position of the upper and lower jaws based on said digital representation of the jaws;

an implant prosthesis program element operating in said at least one digital processor and comprising instructions that cause said at least one digital processor to receive closed jaw position digital simulation information from the digital simulation program element and use the closed jaw position digital simulation information to electronically calculate a space available for placement of an implant prosthesis without contacting opposing teeth in the closed position of the jaws; and a design program element operating in said at least one digital processor and comprising instructions that cause said at least one digital processor to receive space information from the implant prosthesis program element, electronically generate a digital design for automated manufacturing of said implant prosthesis to fit within the space available, generate a digital output defining said digital design, and electronically transmit said digital output to an external element whereby said digital design is used for automated manufacturing of the implant prosthesis.

12. The computer system of claim 11 further comprising analysis software that displays said three-dimensional representation for an expert analyst, receives case-specific input from the expert to define the proposed implant placement, and stores said proposed implant placement in said at least one memory element.

13. The computer system of claim 11 further comprising analysis software operably connected to said at least one digital processor that analyzes said three-dimensional digital representation to generate said proposed implant placement, and stores said proposed implant placement in said at least one memory element.

14. The computer system of claim 11 wherein the digital image data interface stores cone beam imaging data of the target jaw area.

15. The computer system of claim 11 wherein the information defining at least one implant placement stored in said at least one memory element includes a proposed length of an implant post.

* * * * *